US009415087B2

(12) United States Patent
Naoumov et al.

(10) Patent No.: US 9,415,087 B2
(45) Date of Patent: Aug. 16, 2016

(54) COMPOSITIONS AND METHODS FOR TREATING CORONAVIRUS INFECTION

(71) Applicant: LUDWIG-MAXIMILIANS-UNIVERSITAET MUENCHEN, Munich (DE)

(72) Inventors: Nikolai Naoumov, Basel (CH); Albrecht von Brunn, Schwabmuenchen (DE)

(73) Assignee: Ludwig-Maximilians-Universitaet Muenchen, Munich (DE)

( * ) Notice: Subject to any disclaimer, the term of this patent is extended or adjusted under 35 U.S.C. 154(b) by 0 days.

(21) Appl. No.: 14/707,356

(22) Filed: May 8, 2015

(65) Prior Publication Data

US 2016/0082074 A1    Mar. 24, 2016

Related U.S. Application Data

(60) Provisional application No. 61/951,106, filed on Mar. 11, 2014, provisional application No. 61/951,742, filed on Mar. 12, 2014.

(51) Int. Cl.
*A61K 38/13* (2006.01)
*A61K 45/06* (2006.01)
*A61K 31/7056* (2006.01)

(52) U.S. Cl.
CPC .............. *A61K 38/13* (2013.01); *A61K 31/7056* (2013.01); *A61K 45/06* (2013.01)

(58) Field of Classification Search
None
See application file for complete search history.

(56) References Cited

U.S. PATENT DOCUMENTS

2012/0253007 A1   10/2012   Whitaker et al.

OTHER PUBLICATIONS

Carbajo-Lozoya et al. Virus Research. 184, 44-53. 2014.*
Medical Xpress. MedicalXpress.com. "Derivatives of a known drug inhibity the replication of a pathogenic coronavirus." Mar. 18, 2014.*
Koren et al. JAMC. 168(10). 1289-1292. 2003.*
Adedeji, et al., "Evaluation of SSYA10-001 as a Replication Inhibitor of Severe Acute Respiratory Syndrome, Mouse Hepatitis, and Middle East Respiratory Syndrome Coronaviruses", Antimicrobial Agents and Chemotherapy, 58(8):4894, May 2014.
An, et al., "Regulatory Polymorphisms in the Cyclophilin Gene, PPIA, Accelerate Progression to AIDS", PLoS Pathog, 3(6):e88 Jun. 2007.
Arbour, et al., "Neuroinvasion by Human Respiratory Coronaviruses", Journal of Virology, 74(19):8913-8921, Oct. 2000.
Arevalo-Rodriguez, et al., "Cyclophilin A and Ess1 interact with and regulate silencing by the Sin3-Rpd3 histone deacetylase", The EMBO Journal, 19(14):3739-3749, 2000.
Bartenschlager, et al., "Efficient hepatitis C virus cell Culture system: What a difference the host cell makes", PNAS, 102(28):9739-9740, Jul. 12, 2005.
Bigham, et al., "Variants in Host Viral Replication Cycle Genes are Associated with Heterosexual HIV-1 Acquisition in Africa", J. Acquir Immune Defic Syndr, 66(2):127-134, Jun. 2014.
Blight, et al., "Highly Permissive Cell Lines for Subgenomic and Genomic Hepatitis C Virus RNA Replication" Journal of Virology, 76(24):13001-13014, Dec. 2002.
Carbajo-Lozoya, et al., "Replication of human coronaviruses SARS-CoV, HCoV-NL63 and HCoV-229E is inhibited by the drug FK506", Virus Research 165:112-117, Jan. 2012.
Carbajo-Lozoya, et al., "Human coronavirus NL63 replication is cyclophilin A-dependent and inhibited by non-immunosupressive cyclosporine A-derivatives including Alisporivir", Virus Research, 184:44-53, Jan. 2014.
Cervantes-Barragan, et al., "Dendritic Cell-Specific Antigen Delivery by Coronavirus Vaccine Vectors Induces Long-Lasting Protective Antiviral and Antitumor Immunity", mBio, 1(4):e00171-10, Sep./Oct. 2010.
Collins, "In Vitro Detection of Apoptosis in Monocytes/Macrophages Infected with Human Coronavirus", Clinical and Diagnostic Laboratory Immunology, 9(6):1392-1395, Nov. 2002.
De Paulis, et al., "Cyclosporin H is a potent and selective competitive antagonist of human basophil activation by N-formyl-methionyl-leucyl-phenylalanine", J. Allergy Clin. Immunol, 98(1):153-164, Jul. 1996.
Desforges, et al., "HCoV-229E Infects and Activates Monocytes", Adv. Exp. Med. Biol., 581:511-514. 2006.
De Wilde, et al., "Cyclosporin A inhibits the replication of diverse coronaviruses", Journal of General Virology, 92:2542-2548, Jun. 2011.
De Wilde, et al., "Cyclosphilin Inhibitors Block Arterivirus Replication by Interfering with Viral RNA Synthesis", J. Virol., 87(3):1454, Nov. 2012.
De Wilde, et al., "MERS-coronavirus replication induces severe in vitro cytopathology and is strongly inhibited by cyclosporine A or interferon-α treatment", Journal of General Virology, 94:1749-1760, Mar. 2013.
De Wilde, et al., "Screening of an FDA-Approved Compound Library Identifies Four Small-Molecule Inhibitors of Middle East Respiratory Syndrome Coronavirus Replication in Cell Culture", Antimicrob. Agents Chemother. 58(8):4875, May 2014.
Dijkman, et al., "Human Coronavirus NL63 and 229E Seroconversion in Children", Journal of Clinical Microbiology, 46(7):2368-2373, Jul. 2008.
Dijkman, et al., "The dominance of human coronavirus OC43 and NL63 infections in infants", Journal of Clinical Virology, 53:135-139, Nov. 2011.
Dyall, et al., "Repurposing of Clinically Developed Drugs for Treatment of Middle East Respiratory Syndrome Coronavirus Infection", Antimicrobial Agents and Chemotherapy, 58(8):4885, May 2014.

(Continued)

*Primary Examiner* — Amber D Steele
*Assistant Examiner* — Schuyler Milton
(74) *Attorney, Agent, or Firm* — Kilpatrick Townsend & Stockton, LLP

(57) ABSTRACT

The invention relates to the use of non-immunosuppressive cyclophilin inhibitors in the treatment of Coronavirus infection in a patient.

8 Claims, 19 Drawing Sheets

(56) References Cited

OTHER PUBLICATIONS

Feigelstock, et al., "Increased susceptibility of Huh7 cells to HCV replication does not require mutations in RIG-I", Virology Journal, 7:10, Feb. 2010.
Friebe, et al., "Kissing-Loop Interaction in the 3' End of the Hepatitis C Virus Genome Essential for RNA Replication", Journal of Virology, 79(1):380-392, Jan. 2005.
Gallay, et al., "Profile of alisporivir and its potential in the treatment of hepatitis C", Drug Design, Development and Therapy, 7:105-115, 2013.
Gaunt, et al., "Epidemiology and Clinical Presentations of the Four Human Coronaviruses 229E, HKU1, NL63, and OC43 Detected over 3 Years Using a Novel Multiplex Real-Time PCR Method", Journal of Clinical Microbiology, 48(8):2940, Jun. 2010.
Ge, et al., "Isolation and characterization of a bat SARS-like coronavirus that uses the ACE2 receptor", Nature, 503:535-538, Nov. 2013.
Gemmill, et al., "Vanishingly Low Levels of Ess1 Prolyl-isomerase Activity Are Sufficient for Growth in *Saccharomyces cerevisiae*", The Journal of Biological Chemistry, 280(16):15510-15517, Apr. 2005.
Hemida, et al., "Middle East Respiratory Syndrome (MERS) coronavirus seroprevalence in domestic livestock in Saudi Arabia, 2010 to 2013", Euro Surveill., 18(50):pii=20659, Dec. 2013.
Hopkins, et al., "SCY-635, a Novel Nonimmunosuppressive Analog of Cyclosporine That Exhibits Potent Inhibition of Hepatitis C Virus RNA Replication In Vitro", Antimicrobial Agents and Chemotherapy, 54(2):660-672, Feb. 2010.
Huang, et al., "Rapamycins—Mechanism of Action and Cellular Resistance", Cancer Biology & Therapy, 2(3):222-232, May/Jun. 2003.
Huynh, et al., "Evidence Supporting a Zoonotic Origin of Human Coronavirus Strain NL63", Journal of Virology, 86(23):12816, Sep. 2012.
Koren, et al., "Ribavirin in the treatment of SARS: A new trick for an old drug?", Canadian Medical Association or its licensors, 168(10):1289-1292, May 2003.
Koutsoudakis, et al., "The Level of CD81 Cell Surface Expression is a Key Determinant for Productive Entry of Hepatitis C Virus into Host Cells", Journal of Virology, 81(2):588-598, Jan. 2007.
Lafemina, "Alternative Screening Approaches for Discovery of MERS Coronavirus Inhibitors", Antimicrob. Agents Chemother. doi:10.1128/AAC.03406-14, American Society for Microbiology, Jun. 2014.
Lang, et al., "Catalysis of protein folding by prolyl isomerase", Letters to Nature, 329:268-270, Sep. 1987.
Legrue, et al., "Does the Binding of Cyclosporine to Calmodulin Result in Immunosuppression", Science, 234:68-71, Oct. 1986.
Lin, "Curing a viral infection by targeting the host: The example of cyclophilin inhibitors", Antiviral Research, 99:68-77, Jan. 2013.
Ludwig Maximilian University of Munich, "Derivatives of a known drug inhibit the replication of a pathogenic coronavirus", MedicalXpress, http://medicalxpress.com/news/2014-03-derivatives-drug-inhibit-replication-pathogenic.html, Mar. 18, 2014.
Lundin, et al., "Targeting Membrane-Bound Viral RNA Synthesis Reveals Potent Inhibition of Diverse Coronaviruses Including the Middle East Respiratory Syndrome Virus", PLOS, 10(5):e1004166, May 2014.
Luo, et al., "Nucleocapsid protein of SARS coronavirus tightly binds to human cyclophilin A", Biochemical and Biophysical Research Communications, 321:557-565, Jun. 2004.
Malesevic, et al., "Anti-inflammatory Effects of Extracellular Cyclosporins are Exclusively Mediated by CD147", Journal of Medicinal Chemistry, 56:7302-7311, May 2013.
Membreno, et al., "Cyclophilin Inhibitors for Hepatitis C Therapy", Clin Liver Dis, 17:129-139, 2013.
Mesel-Lemoine, et al., "A Human Coronavirus Responsible for the Common Cold Massively Kills Dendritic Cells but Not Monocytes", Journal of Virology, 86(14):7577-7587, Jul. 2012.
Naoumov, "Cyclophilin inhibition as potential therapy for liver disease", Journal of Hepatology, 61:1166-1174, Nov. 2014.
Neuman, et al., "Proteomics Analysis Unravels the Functional Repertoire of Coronavirus Nonstructural Protein 3", Journal of Virology, 82(11):5279-5294, Jun. 2008.
Nigro, et al., "Cyclophilin A: a key player for human disease", Cell Death and Disease, 4, e888, doi:10.1038/cddis.2013.410, Oct. 2013.
Perlman, et al., "Coronaviruses post-SARS: update on replication and pathogenesis", Nature Reviews Microbiology, 7:439-450, Jun. 2009.
Pfefferle, et al., "Distant Relatives of Severe Acute Respiratory Syndrome Coronavirus and Close Relatives of Human Coronavirus 229E in Bats, Ghana", Emerging Infectious Diseases, 15(9):1377-1384, Sep. 2009.
Pfefferle, et al., "The SARS-Coronavirus-Host Interactome: Identification of Cyclophilins as Target for Pan-Coronavirus Inhibitors", PLoS, 7(10):e1002331 Oct. 2011.
Prell, et al., "Fine Tuning the Inhibition Profile of Cyclosporine A by Derivatization of the MeBmt Residue", ChemBioChem, 14:63-65 2013.
Raj, et al., "Dipeptidyl peptisdase 4 is a functional receptor for the emerging human coronavirus-EMC", Letter, 495:251-256, Mar. 2013.
Reusken, et al., "Middle East respiratory syndrome coronavirus neutralizing serum antibodies in dromedary camels: a comparative serological study", LancetInfect Dis, 13:859-866 Oct. 2013.
Riva, et al., Hepatitis C virus and interferon type III (interferon lambda 3/interleukin 28B and interferon lambda 4): genetic basis of susceptibility to infection and response to antiviral treatment, Clinical Microbiology and Infection (Impact Factor: 5.77), doi: 10.1111/1469-0691.12797, Oct. 2014.
Sanglier, et al., "Sanglifehrins A, B, C and D, Novel Cyclophilin-binding Compounds Isolated from *Streptomyces* sp. A92-308110", The Journal of Antibiotics, 52(5):466-473, May 1999.
Sastre, "Differentiation between Human Coronaviruses NL63 and 229E Using a Novel Double-Antibody Sandwich Enzyme-Linked Immunosorbent Assay Based on Specific Monoclonal Antibodies", Clin. Vaccine Immunol., 18(1):113, Nov. 2010.
Sims, et al., "SARS-CoV replication and pathogenesis in an in vitro model of the human conducting airway epithelium", ScienceDirect, 133:33-44, Apr. 2007.
Stadler, et al., "SARS—Beginning to Understand a New Virus", Nature Reviews Microbiology, 1:209-218, Dec. 2003.
Van Der Hoek, et al., "Identification of a new human coronavirus", Nature Medicine, published online, doi:10.1038.nm1024, Mar. 2004.
Van Hemert, et al., The inVitro RNA Synthesizing Activity of the Isolated ARterivirus Replication/Transcription Complex is Dependent on a Host Factor, The Journal of Biological Chemistry, 283(24):16525-16536, Jun. 2008.
Vijgen, et al., "Complete Genomic Sequence of Human Cornoavirus OC43: Molecular Clock Analysis Suggests a Relatively Recent Zoonotic Coronavirus Transmission Event", Journal of Virology, 79(3):1595-1604, Feb. 2005.
Von Hahn, et al., "Hepatocytes that Express Variants of Cyclophilin A are Resistant to HCV Infection and Replication", Gastroenterology, 143(2):439-447, Oct. 2011.
Woo, et al., "Characterization and Complete Genome Sequence of a Novel Coronavirus, Coronavirus HKU1, from Patients with Pneumonia", Journal of Virology, 79(2):884-895, Jan. 2005.
Zhou, et al., "Cyclophilin A and viral infections", Biochemical and Biophysical Research Communications, 424:647-650 Jun. 2012.

\* cited by examiner

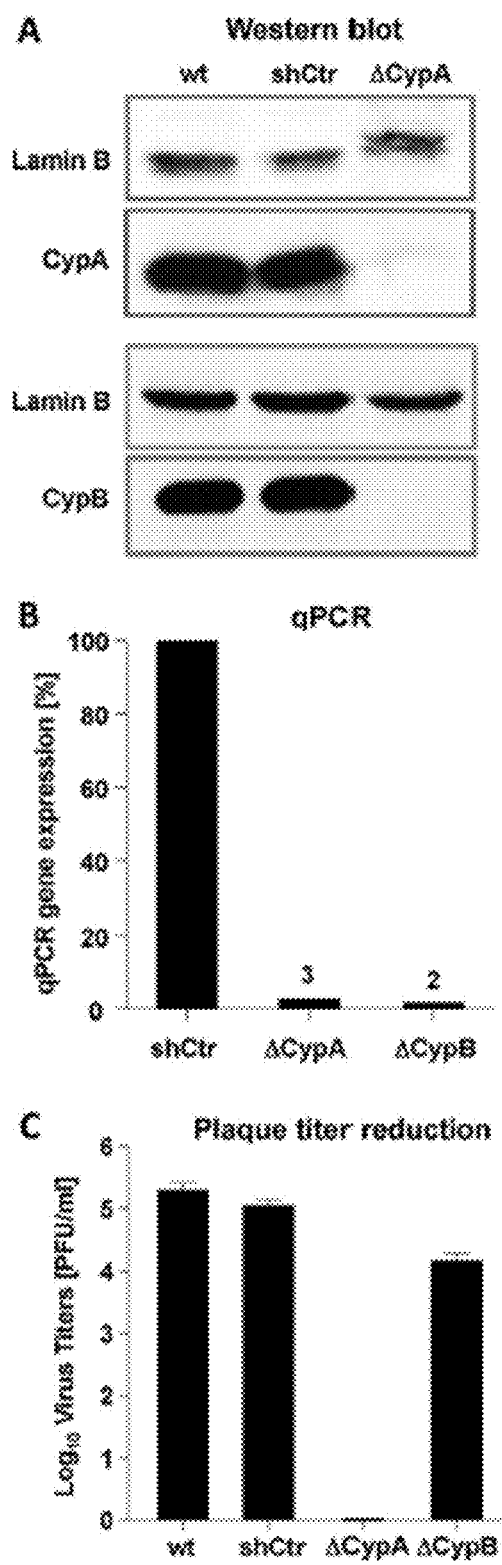
FIGURE 5A-C

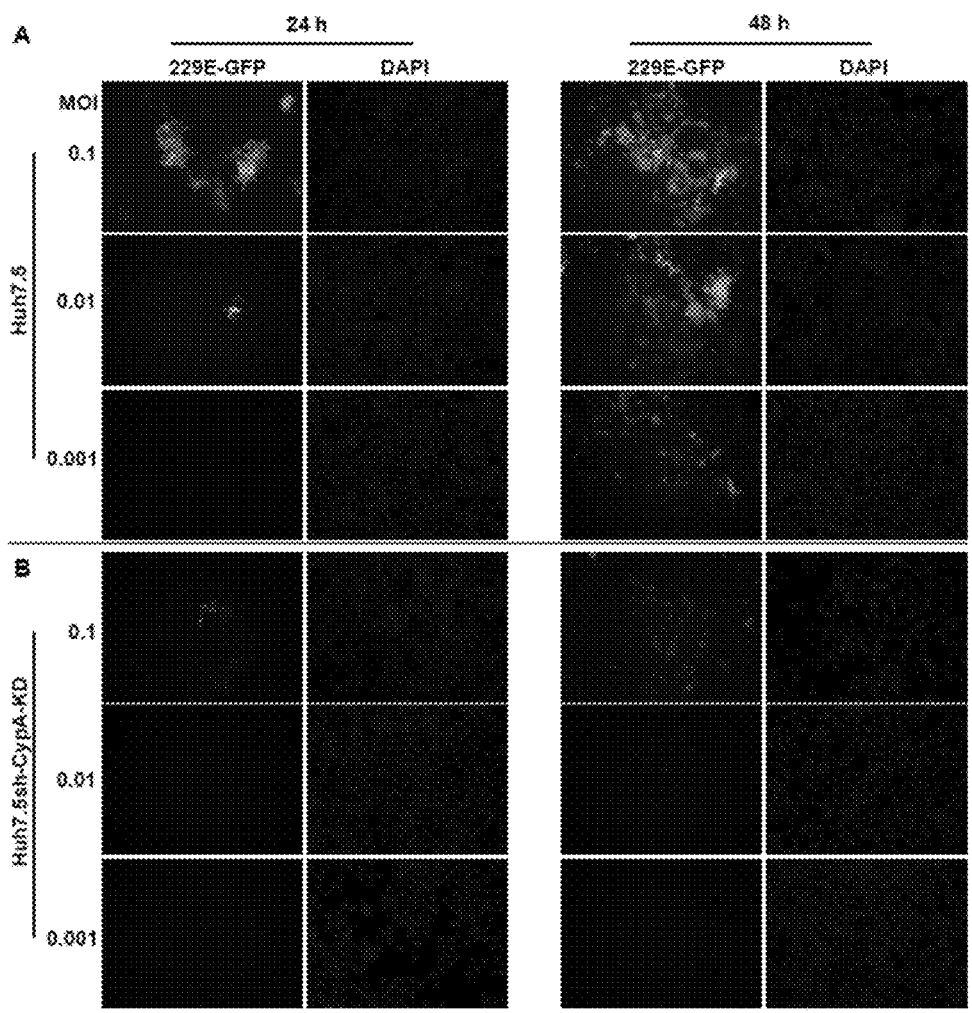
FIGURE 8A-B

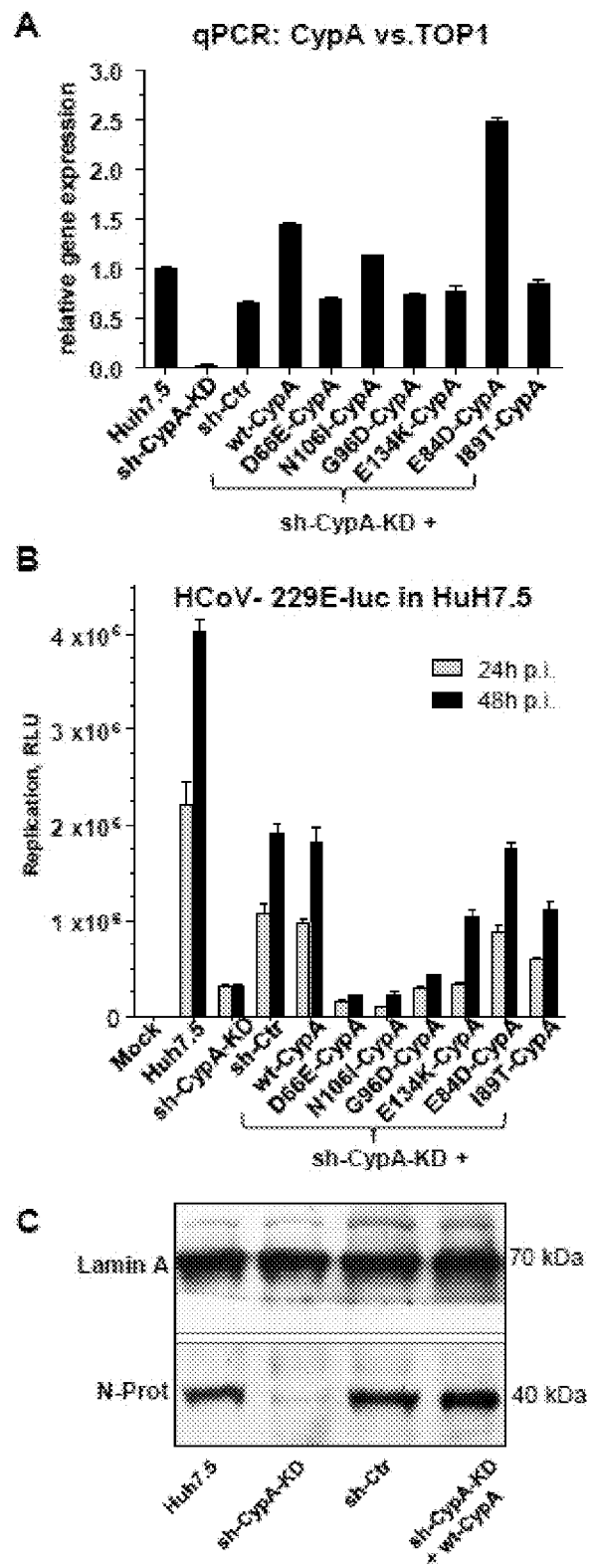
FIGURE 9A-C

FIGURE 10A-B

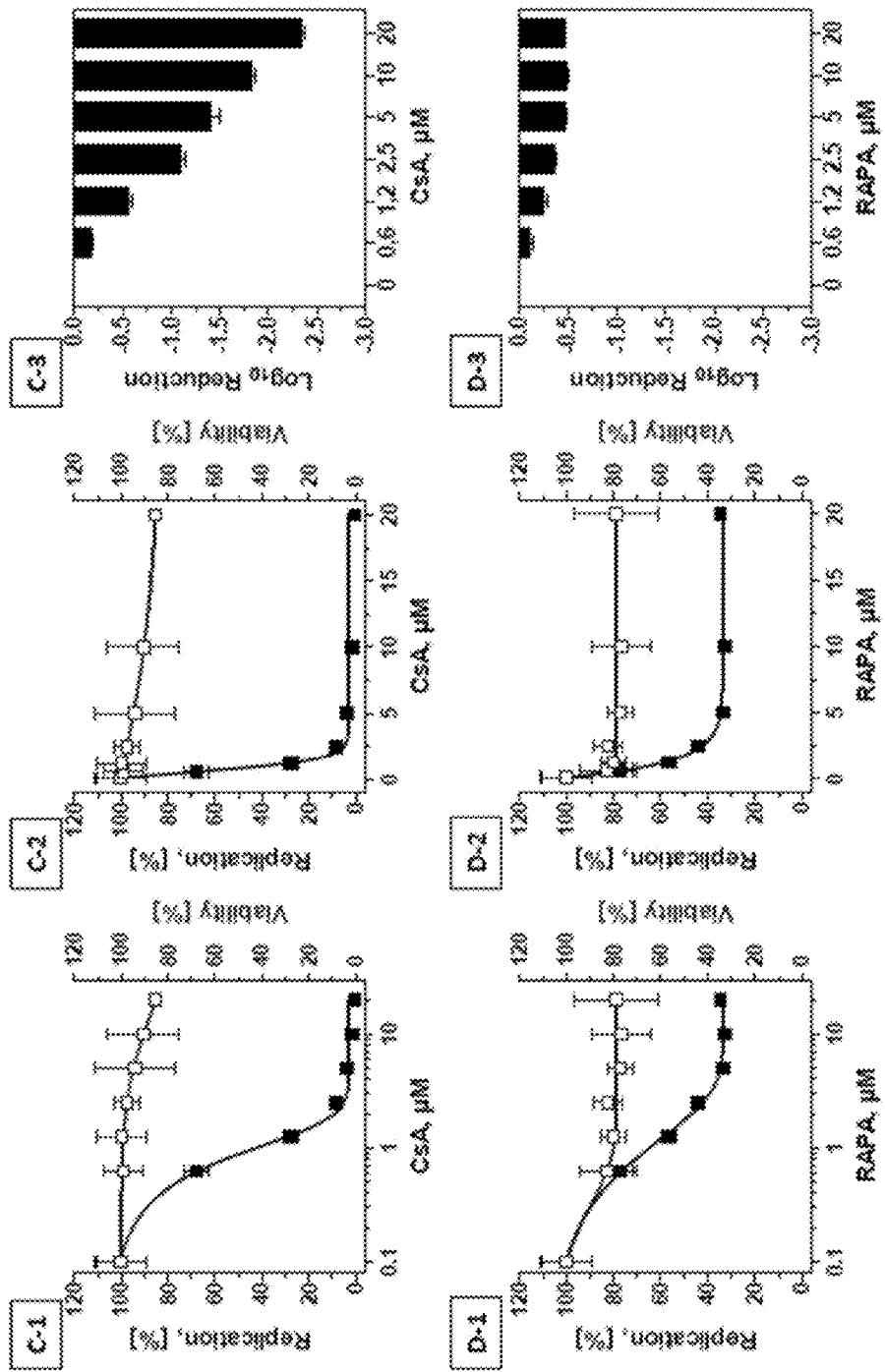
FIGURE 10C-D

FIGURE 11A

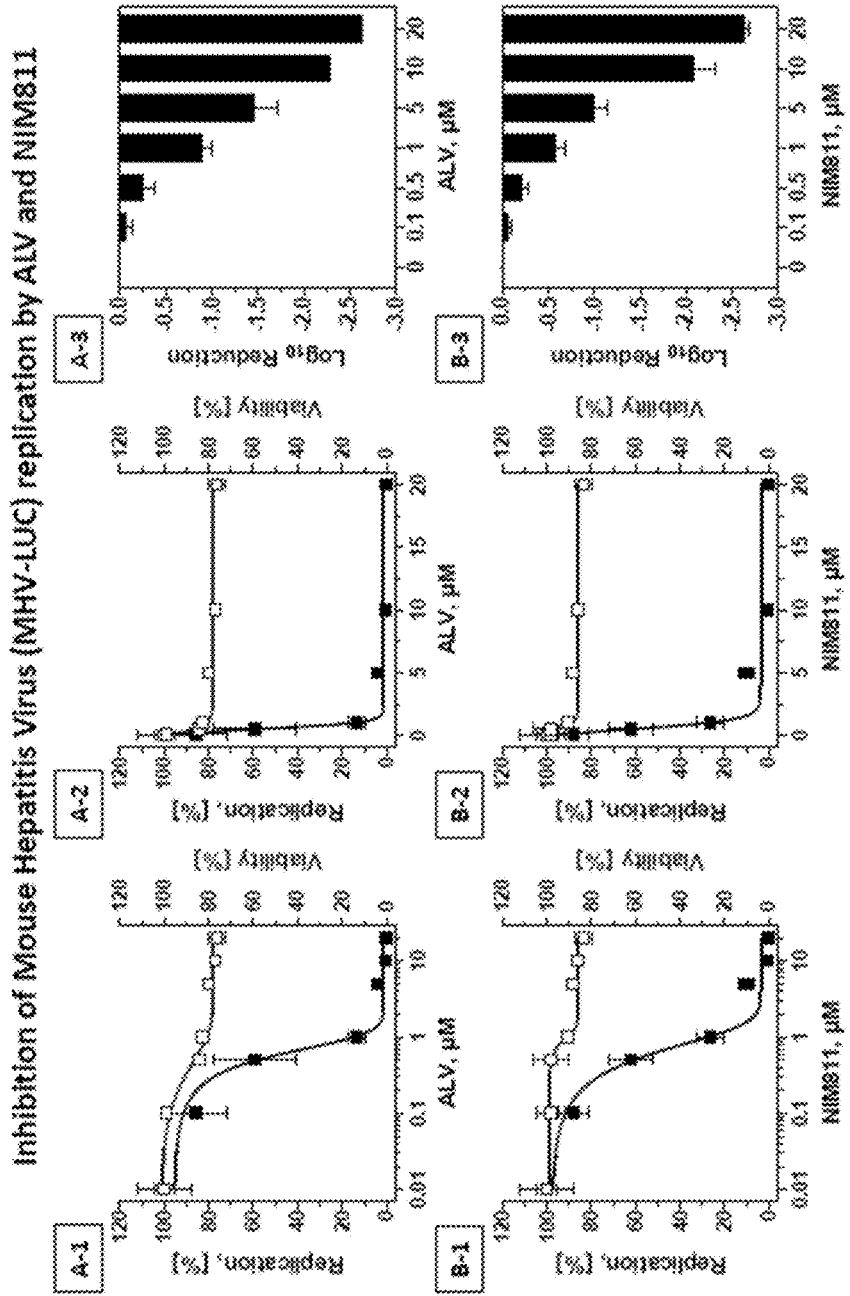
FIGURE 12A-B

SEQUENCE LISTING

<160> NUMBER OF SEQ ID NOS: 10

<210> SEQ ID NO 1
<211> LENGTH: 26
<212> TYPE: DNA
<213> ORGANISM: Artificial sequence
<220> FEATURE:
<223> OTHER INFORMATION: Synthetic construct

<400> SEQUENCE: 1
cttctggtga cgctagtaca gcttat                                           26

<210> SEQ ID NO 2
<211> LENGTH: 25
<212> TYPE: DNA
<213> ORGANISM: Artificial sequence
<220> FEATURE:
<223> OTHER INFORMATION: Synthetic construct

<400> SEQUENCE: 2
agacgtcgtt gtagatccct aacat                                            25

<210> SEQ ID NO 3
<211> LENGTH: 29
<212> TYPE: DNA
<213> ORGANISM: Artificial sequence
<220> FEATURE:
<223> OTHER INFORMATION: Synthetic construct

<400> SEQUENCE: 3
caggttgctt agtgtcccat cagattcat                                        29

<210> SEQ ID NO 4
<211> LENGTH: 58
<212> TYPE: DNA
<213> ORGANISM: Artificial sequence
<220> FEATURE:
<223> OTHER INFORMATION: Synthetic construct

<400> SEQUENCE: 4

-continued ccggcaacaa gatgaagagc accaactcga gttggtgctc ttcatcttgt tgtttttg    58

<210> SEQ ID NO 5
<211> LENGTH: 58
<212> TYPE: DNA
<213> ORGANISM: Artificial sequence
<220> FEATURE:
<223> OTHER INFORMATION: Synthetic construct

<400> SEQUENCE: 5
ccgggttcct gctttcacag aattactcga gtaattctgt gaaagcagga acttttg    58

<210> SEQ ID NO 6
<211> LENGTH: 58
<212> TYPE: DNA
<213> ORGANISM: Artificial sequence
<220> FEATURE:
<223> OTHER INFORMATION: Synthetic construct

<400> SEQUENCE: 6
ccgggttctt catcacgaca gtcaactcga gttgactgtc gtgatgaaga acttttg    58

<210> SEQ ID NO 7
<211> LENGTH: 21
<212> TYPE: DNA
<213> ORGANISM: Artificial sequence
<220> FEATURE:
<223> OTHER INFORMATION: Synthetic construct

<400> SEQUENCE: 7
cagacaaggt cccaaagaca g    21

<210> SEQ ID NO 8
<211> LENGTH: 21
<212> TYPE: DNA
<213> ORGANISM: Artificial sequence
<220> FEATURE:
<223> OTHER INFORMATION: Synthetic construct

<400> SEQUENCE: 8
ttgccatcca accactcagt c    21

<210> SEQ ID NO 9
<211> LENGTH: 21
<212> TYPE: DNA
<213> ORGANISM: Artificial sequence
<220> FEATURE:
<223> OTHER INFORMATION: Synthetic construct

<400> SEQUENCE: 9
ctctccgaac gcaacatgaa g    21

<210> SEQ ID NO 10
<211> LENGTH: 20
<212> TYPE: DNA
<213> ORGANISM: Artificial sequence
<220> FEATURE:
<223> OTHER INFORMATION: Synthetic construct

<400> SEQUENCE: 10
accttgacgg tgactttggg    20

COMPOSITIONS AND METHODS FOR TREATING CORONAVIRUS INFECTION

This application claims the benefit of U.S. Provisional Application No. 61/951,106, filed Mar. 11, 2014 and U.S. Provisional Application No. 61/951,742, filed Mar. 12, 2014, the disclosures of which are both incorporated herein by reference in their entireties.

BACKGROUND

The present disclosure relates to non-immunosuppressive cyclosporin analogues which bind to cyclophilins, which are cyclophilin inhibitors, in particular to their pharmaceutical use in the treatment of infection with Coronaviurs (CoV).

Coronaviruses cause severe diseases of the respiratory and gastrointestinal tract and the central nervous system in animals (Perlman, S., Netland, J., 2009. Coronaviruses post-SARS: update on replication and pathogenesis. Nat. Rev. Microbiol 7(6), 439-450). The infection of humans with HCoV-OC43 and HCoV-229E are known since the mid sixties to be associated with respiratory tract i.e. common cold-like diseases. SARS-CoV (Severe Acute Respiratory Syndrome-Corona Virus) is a highly aggressive human agent, causing the lung disease SARS, with often fatal outcome (Drosten, C., Gunther, S., Preiser, W., van der, W. S., Brodt, H. R., Becker, S., Rabenau, H., Panning, M., Kolesnikova, L., Fouchier, R. A., Berger, A., Burguiere, A. M., Cinatl, J., Eickmann, M., Escriou, N., Grywna, K., Kramme, S., Manuguerra, J. C., Muller, S., Rickerts, V., Sturmer, M., Vieth, S., Klenk, H. D., Osterhaus, A. D., Schmitz, H., Doerr, H. W., 2003. Identification of a novel coronavirus in patients with severe acute respiratory syndrome. N. Engl. J. Med. 348(20), 1967-1976). This virus appeared as an epidemic in 2003 after it had crossed the species barrier from bats to civet cats and humans demonstrating the potential of coronaviruses to cause high morbidity and mortality in humans (Lau, S. K., Woo, P. C., Li, K. S., Huang, Y., Tsoi, H. W., Wong, B. H., Wong, S. S., Leung, S. Y., Chan, K. H., Yuen, K. Y., 2005. Severe acute respiratory syndrome coronavirus-like virus in Chinese horseshoe bats. Proc Natl Acad Sci USA 102(39), 14040-14045; Li, W., Shi, Z., Yu, M., Ren, W., Smith, C., Epstein, J. H., Wang, H., Crameri, G., Hu, Z., Zhang, H., Zhang, J., McEachern, J., Field, H., Daszak, P., Eaton, B. T., Zhang, S., Wang, L. F., 2005. Bats are natural reservoirs of SARS-like coronaviruses. Science 310(5748), 676-679). As no treatment was available, the epidemic could eventually be controlled by highly effective traditional public health measures of quarantine and case isolation. The strains HCoV-NL63 and HCoV-HKU1 were discovered in 2004 and 2005, respectively (van der Hoek, L., Pyrc, K., Jebbink, M. F., Vermeulen-Oost, W., Berkhout, R. J., Wolthers, K. C., Wertheim-van Dillen, P. M., Kaandorp, J., Spaargaren, J., Berkhout, B., 2004. Identification of a new human coronavirus. Nat Med 10(4), 368-373; Woo, P. C., Lau, S. K., Chu, C. M., Chan, K. H., Tsoi, H. W., Huang, Y., Wong, B. H., Poon, R. W., Cai, J. J., Luk, W. K., Poon, L. L., Wong, S. S., Guan, Y., Peiris, J. S., Yuen, K. Y., 2005. Characterization and complete genome sequence of a novel coronavirus, coronavirus HKU1, from patients with pneumonia. Journal of virology 79(2), 884-895). They cause more severe lower respiratory tract infections like bronchiolitis and pneumonia especially in young children, immunocompromised patients and the elderly (van der Hoek, L., 2007. Human coronaviruses: what do they cause? Antivir Ther 12(4 Pt B), 651-658). In 2012, a new human CoV MERS (Middle East Respiratory Syndrome virus, previously called "EMC") emerged from the Middle East with clinical outcomes such as renal failure and acute pneumonia, similar to those of SARS-CoV but with an even higher mortality rate of about 50% (de Groot, R. J., Baker, S. C., Baric, R. S., Brown, C. S., Drosten, C., Enjuanes, L., Fouchier, R. A., Galiano, M., Gorbalenya, A. E., Memish, Z., Perlman, S., Poon, L. L., Snijder, E. J., Stephens, G. M., Woo, P. C., Zaki, A. M., Zambon, M., Ziebuhr, J., 2013. Middle East Respiratory Syndrome Coronavirus (MERS-CoV); Announcement of the Coronavirus Study Group. Journal of virology; van Boheemen, S., de Graaf, M., Lauber, C., Bestebroer, T. M., Raj, V. S., Zaki, A. M., Osterhaus, A. D., Haagmans, B. L., Gorbalenya, A. E., Snijder, E. J., Fouchier, R. A., 2012. Genomic characterization of a newly discovered coronavirus associated with acute respiratory distress syndrome in humans. MBio 3(6); Zaki, A. M., van Boheemen, S., Bestebroer, T. M., Osterhaus, A. D., Fouchier, R. A., 2012. Isolation of a novel coronavirus from a man with pneumonia in Saudi Arabia. N Engl J Med 367(19), 1814-1820).

Human coronaviruses cause approximately 10-15% of all upper and lower respiratory tract infections. They account for significant hospitalizations of children under 18 years of age, the elderly and immunocompromised individuals. According to a number of international studies 5-10% of the acute respiratory diseases are caused by HCoV-NL63 [for review see Abdul-Rasool, S., Fielding, B. C., 2010. Understanding Human Coroonavirus HCoV-NL63. The Open Virology Journal 4, 76-84]. These numbers are probably a great underestimation since during diagnostic screening for respiratory viruses tests for HCoV's are frequently not included. An important aspect HCoV-NL63 infection is the co-infection with other human coronaviruses, influenza A, respiratory syncytial virus (RSV), parainfluenza virus human metapneumovirus (Abdul-Rasool, S., Fielding, B. C., 2010. Understanding Human Coroonavirus HCoV-NL63. The Open Virology Journal 4, 76-84). In children they are associated with acute respiratory tract illness, pneumonia and Croup leading in many cases to hospitalization. In a recent epidemiological study out of 1471 hospitalized children (<2 years) 207 (14%) were HCoV-positive (Dijkman, R., Jebbink, M. F., Gaunt, E., Rossen, J. W., Templeton, K. E., Kuijpers, T. W., van der Hoek, L., 2012. The dominance of human coronavirus OC43 and NL63 infections in infants. Journal of clinical virology: the official publication of the Pan American Society for Clinical Virology 53(2), 135-139). Infection frequencies in children with mild symptoms and in hospitalized children occurred in the order HCoV-OC43>HCoV-NL63>HCoV-HKU1>HCoV-229E. In a large-scale survey on 11,661 diagnostic respiratory samples collected in Edinburgh, UK, between 2006 and 2009, 267 (2.30%) were positive for at least one coronavirus accounting for 8.15% of all virus detections (Gaunt, E. R., Hardie, A., Claas, E. C., Simmonds, P., Templeton, K. E., 2010. Epidemiology and clinical presentations of the four human coronaviruses 229E, HKU1, NL63, and OC43 detected over 3 years using a novel multiplex real-time PCR method. Journal of clinical microbiology 48(8), 2940-2947). 11 to 41% of coronaviruses detected were present in samples tested positive for other respiratory viruses (e.g. RSV).

Although inhibitors of coronavirus enzymes (reviewed by (Tong, T. R., 2009a. Therapies for coronaviruses. Part 2: Inhibitors of intracellular life cycle. Expert. Opin. Ther. Pat 19(4), 415-431; Tong, T. R., 2009b. Therapies for coronaviruses. Part I of II—viral entry inhibitors. Expert. Opin. Ther. Pat 19(3), 357-367) and compounds inhibiting in vitro replication have been described (Kono, M., Tatsumi, K., Imai, A. M., Saito, K., Kuriyama, T., Shirasawa, H., 2008. Inhibition of human coronavirus 229E infection in human epithelial lung cells (L132) by chloroquine: involvement of p38 MAPK and ERK. Antiviral research 77(2), 150-152; to Velthuis, A. J., van den Worm, S. H., Sims, A. C., Baric, R. S., Snijder, E. J., van Hemert, M. J., 2010. Zn(2+) inhibits coronavirus and arterivirus RNA polymerase activity in vitro and zinc ionophores block the replication of these viruses in cell culture. PLoS Pathog 6(11), e1001176; Vincent, M. J., Bergeron, E., Benjannet, S., Erickson, B. R., Rollin, P. E., Ksiazek, T. G., Seidah, N. G., Nichol, S. T., 2005. Chloroquine is a potent inhibitor of SARS coronavirus infection and spread. Virol J 2, 69), clinically licensed antivirals for coronavirus infection are absent. Coronaviruses represent the largest group of single-stranded RNA viruses with plus strand orientation. Thus they are prone to evolutionary change due to lack of proof reading activity of its polymerases provoking the development of resistance mutations in the presence of inhibitors of viral proteins. Virus replication depends on a variety of host factors (de Haan, C. A., Rottier, P. J., 2006. Hosting the severe acute respiratory syndrome coronavirus: specific cell factors required for infection. Cellular microbiology 8(8), 1211-1218; Vogels, M. W., van Balkom, B. W., Kaloyanova, D. V., Batenburg, J. J., Heck, A. J., Helms, J. B., Rottier, P. J., de Haan, C. A., 2011. Identification of host factors involved in coronavirus replication by quantitative proteomics analysis. Proteomics 11(1), 64-80; Wang, R. Y., Li, K., 2012. Host factors in the replication of positive-strand RNA viruses. Chang Gung medical journal 35(2), 111-124) which represent potential antiviral targets. These might be more preferable targets than viral proteins as development of resistance is much less likely.

In a recent study we performed a genome-wide SARS-CoV yeast-two-hybrid interaction screen with human cDNA libraries identifying human immunophilins (including cyclophilins [Cyps] and FK506-binding proteins [FKBPs] as interaction partners of CoV non-structural protein 1 [Nsp1](Pfefferle, S., Schopf, J., Kogl, M., Friedel, C. C., Muller, M. A., Carbajo-Lozoya, J., Stellberger, T., von Dall'Armi, E., Herzog, P., Kallies, S., Niemeyer, D., Ditt, V., Kuri, T., Zust, R., Pumpor, K., Hilgenfeld, R., Schwarz, F., Zimmer, R., Steffen, I., Weber, F., Thiel, V., Herrler, G., Thiel, H. J., Schwegmann-Wessels, C., Pohlmann, S., Haas, J., Drosten, C., von Brunn, A., 2011. The SARS-coronavirus-host interactome: identification of cyclophilins as target for pan-coronavirus inhibitors. PLoS Pathog 7(10), e1002331). A pronounced feature of most mammalian cyclophilins is their ability to bind the immunosuppressive drug cyclosporine A (CsA). We showed that the drug acts as a replication inhibitor of a number of human (SARS-CoV, HCoV-NL63 and HCoV-229E) and animal coronaviruses (Feline CoV [serotypes I and II], porcine transmissible gastroenteritis virus (TGEV), and avian infectious bronchitis virus [IBV]) suggesting host cyclophilins as targets for pan-coronavirus inhibition (Pfefferle, S., Schopf, J., Kogl, M., Friedel, C. C., Muller, M. A., Carbajo-Lozoya, J., Stellberger, T., von Dall'Armi, E., Herzog, P., Kallies, S., Niemeyer, D., Ditt, V., Kuri, T., Zust, R., Pumpor, K., Hilgenfeld, R., Schwarz, F., Zimmer, R., Steffen, I., Weber, F., Thiel, V., Herrler, G., Thiel, H. J., Schwegmann-Wessels, C., Pohlmann, S., Haas, J., Drosten, C., von Brunn, A., 2011. The SARS-coronavirus-host interactome: identification of cyclophilins as target for pan-coronavirus inhibitors. PLoS Pathog 7(10), e1002331). Inhibition of SARS-CoV, HCoV-229E and in addition of MHV was subsequently also confirmed by de Wilde et al. (de Wilde, A. H., Zevenhoven-Dobbe, J. C., van der Meer, Y., Thiel, V., Narayanan, K., Makino, S., Snijder, E. J., van Hemert, M. J., 2011. Cyclosporin A inhibits the replication of diverse coronaviruses. The Journal of general virology 92(Pt 11), 2542-2548). Inhibition of feline CoV replication was also found by Tanaka et al. (Tanaka, Y., Sato, Y., Osawa, S., Inoue, M., Tanaka, S., Sasaki, T., 2012. Suppression of feline coronavirus replication in vitro by cyclosporin A. Veterinary research 43(1), 41). Similarly, we showed that FK506 inhibits the replication of SARS-CoV, HCoV-NL63 and HCoV-229E and the dependence of HCoV-NL63 on FKBP1A/B Carbajo-Lozoya, J., Muller, M. A., Kallies, S., Thiel, V., Drosten, C., von Brunn, A., 2012. Replication of human coronaviruses SARS-CoV, HCoV-NL63 and HCoV-229E is inhibited by the drug FK506. Virus Res 165(1), 112-117).

Cyclophilins and FKBPs represent large, independent families of peptidyl-prolyl cis/trans isomerases (PPIases, EC number 5.2.1.8) thus exerting important functions on folding, maturation and trafficking of proteins within the eukaryotic cell (Blackburn, E. A., Walkinshaw, M. D., 2011. Targeting FKBP isoforms with small-molecule ligands. Current opinion in pharmacology 11(4), 365-371; Davis, T. L., Walker, J. R., Campagna-Slater, V., Finerty, P. J., Paramanathan, R., Bernstein, G., MacKenzie, F., Tempel, W., Ouyang, H., Lee, W. H., Eisenmesser, E. Z., Dhe-Paganon, S., 2010. Structural and biochemical characterization of the human cyclophilin family of peptidyl-prolyl isomerases. PLoS Biol 8(7), e1000439). Both CsA and FK-506 act as tight-binding, reversible and competitive inhibitors of the active site of these enzymes (Fischer, G., Wittmann-Liebold, B., Lang, K., Kiefhaber, T., Schmid, F. X., 1989. Cyclophilin and peptidyl-prolyl cis-trans isomerase are probably identical proteins. Nature 337(6206), 476-478). Physical interaction of cyclophilins with viral proteins, and thus replication sensitivity to CsA have been shown for several viruses, e.g. the capsid proteins of HIV-1 (Strebel, K., Luban, J., Jeang, K. T., 2009. Human cellular restriction factors that target HIV-1 replication. BMC Med 7, 48; Ylinen, L. M., Schaller, T., Price, A., Fletcher, A. J., Noursadeghi, M., James, L. C., Towers, G. J., 2009. Cyclophilin A levels dictate infection efficiency of human immunodeficiency virus type 1 capsid escape mutants A92E and G94D. Journal of virology 83(4), 2044-2047) and HPV types 16 (Bienkowska-Haba, M., Patel, H. D., Sapp, M., 2009. Target cell cyclophilins facilitate human papillomavirus type 16 infection. PLoS Pathog 5(7), e1000524), the N protein of Vesicular stomatitis Virus (Bose, S., Mathur, M., Bates, P., Joshi, N., Banerjee, A. K., 2003. Requirement for cyclophilin A for the replication of vesicular stomatitis virus New Jersey serotype. The Journal of general virology 84(Pt 7), 1687-1699), the NS5a of HCV (Fernandes, F., Ansari, I. U., Striker, R., 2010. Cyclosporine inhibits a direct interaction between cyclophilins and hepatitis C NS5A. PloS one 5(3), e9815; Fischer, G., Wittmann-Liebold, B., Lang, K., Kiefhaber, T., Schmid, F. X., 1989. Cyclophilin and peptidyl-prolyl cis-trans isomerase are probably identical proteins. Nature 337(6206), 476-478), the NS4A protein of the mosquito-borne Japanese encephalitis virus (Kambara, H., Tani, H., Mori, Y., Abe, T., Katoh, H., Fukuhara, T., Taguwa, S., Moriishi, K., Matsuura, Y., 2011. Involvement of cyclophilin B in the replication of Japanese encephalitis virus. Virology 412(1), 211-219), the NS5 protein of West Nile virus (Qing, M., Yang, F., Zhang, B., Zou, G., Robida, J. M., Yuan, Z., Tang, H., Shi, P. Y., 2009. Cyclosporine inhibits flavivirus replication through blocking the interaction between host cyclophilins and viral NS5 protein. Antimicrobial agents and chemotherapy 53(8), 3226-3235) and the M1 protein of influenza A virus (Liu, X., Sun, L., Yu, M., Wang, Z., Xu, C., Xue, Q., Zhang, K., Ye, X., Kitamura, Y., Liu, W., 2009. Cyclophilin A interacts with influenza A virus M1 protein and impairs the early stage of the viral replication. Cellular microbiology 11(5), 730-741). The most prominent cyclophilins thought to be involved are CypA and CypB. PPIase-independent activities of CsA and FK506 exerted by gain-of-function, result from the binary complexes formed by binding of the drugs to Cyps and FKBPs, respectively. Based on the inhibition of the protein phosphatase activity of calcineurin, these complexes block the cellular calcineurin (CaN)/NFAT pathway thereby interfering with T-cell activation and 11-2 production. Chemically changed derivatives covering specific side-chain modifications, the so-called non-immunosuppressive cyclosporine- or FK506, analogues, can discriminate between alternative signalling pathways either based on PPIase- or CaN-inhibiting functions.

Identifying the interaction of the SARS-CoV Nsp1 protein with Cyps and FKBPs, and the sensitivity of CoV replication to both drugs, CsA and FK506, CsA was suggested as a potential pan-CoV inhibitor (Pfefferle, S., Schopf, J., Kogl, M., Friedel, C. C., Muller, M. A., Carbajo-Lozoya, J., Stellberger, T., von Dall'Armi, E., Herzog, P., Kallies, S., Niemeyer, D., Ditt, V., Kuri, T., Zust, R., Pumpor, K., Hilgenfeld, R., Schwarz, F., Zimmer, R., Steffen, I., Weber, F., Thiel, V., Herrler, G., Thiel, H. J., Schwegmann-Wessels, C., Pohlmann, S., Haas, J., Drosten, C., von Brunn, A., 2011. The SARS-coronavirus-host interactome: identification of cyclophilins as target for pan-coronavirus inhibitors. PLoS Pathog 7(10), e1002331). Here it is demonstrated that, by using Alisporivir, NIM811 and a series of newly synthesized CsA and FK506 derivatives, inhibition of HCoV-NL63 replication independent of the immunosuppressive character of the compounds. It is further shown that CypA but not CypB is required for virus replication.

The cyclosporins and the non-immunosuppressive analogues comprise a class of structurally distinctive, cyclic, poly-N-methylated undecapeptides, commonly possessing pharmacological, in particular immunosuppressive, or anti-inflammatory activity. The first of the cyclosporins to be isolated was the naturally occurring fungal metabolite Ciclosporin or Cyclosporine, also known as cyclosporin A (CsA). Cyclosporins which bind strongly to cyclophilin but are not immunosuppressive have been identified. PCT/EP 2004/009804, WO 2005/021028, or WO 2006/071619 (which are incorporated by reference herein in their entirety) disclose non-immunosuppressive cyclosporins which bind to cyclophilin and have also been found to have an inhibitory effect on Hepatitis C virus (HCV). WO 2006/038088, incorporated herein by reference in its entirety, describes methods and compositions for the use of alisporivir in the treatment of HCV. Alisporivir (DEB025 or Debio-025) is a cyclophilin (Cyp) inhibitor and its mode of action as an anti-HCV agent is via inhibition of host proteins, in particular of cyclophilin A, that are directly involved in HCV replication.

Therefore it is an object of the present disclosure to provide new methods for the treatment of patients with Coronavirus infection alone or patients infected co-infected with an additional Coronavirus.

Surprisingly it has been found that non-immunosupressive cyclophilin inhibitors, in particular alisporivir and NIM811, have antiviral properties against Coronavirus that can be used effectively in the treatment of CoV infections. In particular, it has been found that the non-immunosuppressive cyclophilin inhibitors alisporivir and NIM811 inhibit CoV replication independent of the immunosuppressive character of the compounds. Accordingly, the present invention provides new anti-CoV treatments using alisporivir and NIM811.

Furthermore, the present disclosure provides methods for the treatment of CoV and CoV-co-infections comprising administering an effective amount of a non-immunosuppressive cyclophilin inhibitor, in particular alisporivir and/or NIM811, either alone or in combination with another antiviral agent such as ribavirin.

SUMMARY

Provided herein is a method for treating Coronavirus infection in a patient, comprising administering to said patient a non-immunosuppressive cyclophilin inhibitor, in particular alisporivir and/or NIM811, either alone or in combination with another antiviral agent such as ribavirin.

Also provided is a method for inhibiting Coronavirus growth, comprising administering a non-immunosuppressive cyclophilin inhibitor, in particular alisporivir and/or NIM811, either alone or in combination with another antiviral agent such as ribavirin.

Further provided is the use of alisporivir and/or NIM811 in the preparation of a pharmaceutical composition for use in any method as defined above. Also provided is the use of alisporivir and/or NIM811 in the preparation of a medicament for use in any method as defined above. Further provided is the use of alisporivir and/or NIM811 in combination with a direct antiviral agent that inhibits Coronavirus growth in the preparation of a medicament for use in any method as defined above.

BRIEF DESCRIPTION OF DRAWINGS

FIGS. 5A-C depict the characterization of CypA and CypB in Caco-2 knockdown cells and growth analysis of HCoV-NL63. CypA and CypB expression was determined by Western blot using an anti-CypA and anti-CypB (A) antibody and by qPCR (B). Lamin B was detected with an anti-lamin B antibody as a loading control. hTOP1 was used in qPCR to standardize cyclophilin expression. Growth of HCoV-NL63 on Caco-2 wt, Caco-2 shCtr non-target cells, Caco-2 ΔCypA (CypA KD) and Caco-2 ΔCypB (CypB KD) knockdown mutants was analysed by plaque titration assay (C). Virus titers are depicted in (D). Mock infections are not shown.

FIGS. 8A-C show growth analysis of HCoV-229E-GFP in Huh-7.5 and Huh-7.5-sh-CypA-KD cells at different MOIs. FIGS. 8A-B show GFP fluorescence quantification of representative fields chosen arbitrarily at 24 and 48 h timepoints (magnification 200× plus) in Huh-7.5 and Huh-7.5-sh-CypA-KD cells, respectively. FIG. 8C demonstrates reduction of 229E N-protein expression (mouse anti-N mab) as a measure of viral replication in Huh-7.5-sh-CypA-KD in comparison to Huh-7.5 cells. A rabbit anti-Lamin A antibody detected Lamin A as a loading control.

FIGS. 9A-C show replication analysis of HCoV-229E-LUC in Huh-7.5-KD and single SNP variant mutants. (A) qPCR analysis of CypA expression in sh-CypA-KD, non-target control (sh-Ctr) and with wtCypA reconstituted sh-CypA-KD cells, as well as sh-CypA-KD cells reconstituted with CypA SNP variants carrying amino acid exchanges at D66E, N106I, G96D, E134K, E84D and I89T. hTOP1 was used in qPCR to standardize cyclophilin expression. (B) Replication was measured by determining Renilla Luciferase activity in cell extracts after 24 and 48 hrs p.I. Values are given as relative light units (RLU). (C) HCoV-229E-LUC N-protein analysis in Huh-7.5, sh-CypA-KD, non-target control (sh-Ctr) and with wtCypA reconstituted Huh-7.5 cells.

FIG. 10A-D shows effect of CsA and various non immunosuppressive derivatives (ALV, NIM811) on FCoVLUC (MOI=0.1) replication in Felis catus whole fetus (fcwf) cells determined by Renilla luciferase activity measurement. Left Y-axes represent the percentage of reduction of virus replication in linear (left and middle panels) or in log scale (right panels) at the indicated inhibitor concentrations given on the X-axis (log scale: left panels; linear scale: middle and right panels). Cell viability with mock-treated cells set to 100% are shown on the right Y-axes of the left and middle panels. Measurements were taken 24 hrs p.I. RAPA targets an unrelated cellular pathway and served as negative control. The graphs were plotted using Prism 5 (GraphPad Software, Inc.) and by a non-linear regression with a variable slope algorithm, the curve was fitted for each respective inhibitor and the EC50 was calculated. Fcwf cells were seeded 24 hours prior to infection with Feline Coronavirus expressing Renilla luciferase (FCoV-LUC) in 48-well format (triplicated values). Cells were infected at MOI (Multiplicity of Infection)= 0.1 for two hours at 370 C. Virus inoculum was washed off twice with PBS (Phosphate buffered saline) and cells were incubated with various inhibitor concentrations (diluted in 1% EtOH/DMEM). 24 hours post infection (pI) Renilla luminescence was measured in cell lysates using Renilla Luciferase Assay (Promega GmbH). Cell viability (Cell Titer-Glo, Promega GmbH) was determined as a measure of ATP-content of cells in parallel experimental settings at same conditions but without virus infection.

FIGS. 11A-B show inhibition of SARS-CoV-RNA replicon propagation by ALV and NIM811 in BHK-21 cells. BHK-21 cells were transfected by electroporation with SARS-CoV-Replicon RNA expressing Metridia Luciferase. 5 μg in vitro transcribed Replicon-RNA and 0.4 μg in vitro transcribed N-RNA dissolved in 100 μl OptiMEM (Life Technologies) were electroporated into BHK21 cells. 2×104 cells per well were seeded in a 48-well format in triplicates containing 100 ng Replicon-RNA and 8 ng N-RNA per well. After 20 hours luminiscence from cell supernatant was determined by Renilla Luciferase Assay System (Promega GmbH). Data were plotted as mean±SD of triplicate samples using Prism 5 (GraphPad Software, Inc.) and by a non-linear regression with a variable slope algorithm, the curve was fitted for each respective inhibitor and the EC50 was calculated.

FIGS. 12A-C show inhibition of Mouse Hepatitis Virus replication by non-immunosuppressive CsA (Cyclosporin A) derivatives ALV (Alisporivir) and NIM811 Effect of CsA and various non-immunosuppressive derivatives (ALV, NIM811) on MHVLUC replication in L929 cells determined by Gausseria luciferase activity measurement. Left Y-axes represent the percentage of reduction of virus replication in linear (left and middle panels) or in log scale (right panels) at the indicated inhibitor concentrations given on the X-axis (log scale: left panels; linear scale: middle and right panels). Cell viability with mock-treated cells set to 100% are shown on the right Y-axes of the left and middle panels. Measurements were taken 48 hrs post infection (p.I.). RAPA targets an unrelated cellular pathway and served as negative control. The graphs were plotted using Prism 5 (GraphPad Software, Inc.) and by a non-linear regression with a variable slope algorithm, the curve was fitted for each respective inhibitor and the EC50 was calculated. Fcwf cells were seeded 24 hours prior to infection with Mouse Hepatitis Virus expressing Gausseria luciferase (MHV-LUC) in 48-well format (duplicates). Cells were infected at MOI (Multiplicity of Infection)=0.1 for two hours at 370 C. Virus inoculum was washed off twice with PBS (Phosphate buffered saline) and cells were incubated with various inhibitor concentrations (diluted in 1% EtOH/DMEM). 24 hours p.I. Renilla luminescence was measured in cell lysates using Renilla Luciferase Assay (Promega GmbH). Cell viability (Cell Titer-Glo, Promega GmbH) was determined as a measure of ATP-content of cells in parallel experimental settings at same conditions but without virus infection.

DETAILED DESCRIPTION

Figure 1:
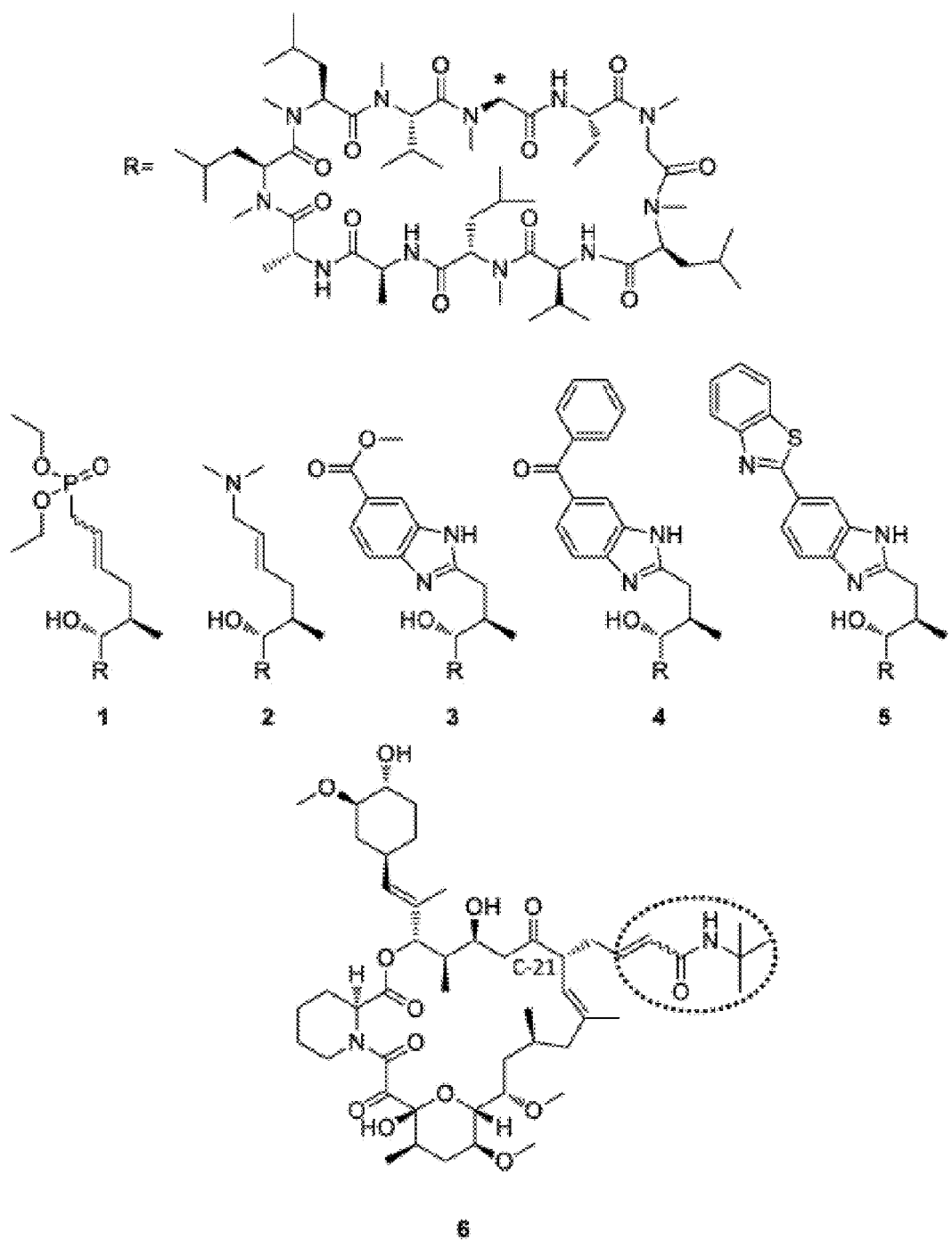
FIG. 1 depicts chemical structures of novel CsA derivatives (compounds 1-5) and the FK506 derivative compound 6) used in this work. The position where the R substituents are attached to the CsA ring core at position 1 is marked with an asterisk. Parent FK506 is substituted at position C-21.

As used herein a "Cornonavirus infection" means an infection, including a patient being infected, with any Coronavirus virus including human coronavirus HCoV-NL63, HCoV-OC43, HCoV-229E, HCoV-HKU1, SARS-CoV (Severe Acute Respiratory Syndrome-Corona Virus), and CoV MERS (Middle East Respiratory Syndrome virus, previously called "EMC").

As used herein, "microgram/kilogram" means microgram drug per kilogram body weight of the mammal, including human, to be treated.

As used herein, the term "treatment" or "treat" refer to both prophylactic or preventative treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment.

By "therapeutic regimen" is meant the pattern of treatment of an illness, e.g., the pattern of dosing used during Coronavirus therapy. A therapeutic regimen may include an induction regimen and a maintenance regimen.

The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both.

The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein, the term "about", unless the context dictates otherwise, is used to mean a range of + or −10%.

As used throughout, a subject can be a vertebrate, more specifically a mammal (e.g., a human, horse, cat, dog, cow, pig, sheep, goat, mouse, rabbit, rat, and guinea pig). The term does not denote a particular age or sex. Thus, adult and newborn subjects, whether male or female, are intended to be covered. As used herein, patient or subject may be used interchangeably and can refer to a subject with or at risk of developing a Coronavirus infection. The term patient or subject includes human and veterinary subjects.

In some embodiments, a non-immunosuppressive cyclophilin inhibitor, in particular alisporivir and/or NIM811 is used in the treatment of Coronavirus infection in a patient. In still another aspect, a non-immunosuppressive cyclophilin inhibitor, in particular alisporivir and/or NIM811, either alone or in combination with another antiviral agent such as ribavirin is administered.

In another embodiment, a pharmaceutical composition comprising a non-immunosuppressive cyclophilin inhibitor, in particular alisporivir and/or NIM811, either alone or in combination with another antiviral agent such as ribavirin for use according to any of the methods disclosed herein and a package comprising said pharmaceutical composition in combination with instructions to administer said composition is described.

In another embodiment, a non-immunosuppressive cyclophilin inhibitor, in particular alisporivir and/or NIM811 may be administered with additional agents of the standard of care that promote the antiviral efficacy of the therapy treatment. Direct antiviral agent, is used herein to mean agents that interfere with specific steps in the Coronavirus replication cycle.

In treatment described above effective dosages of the standard of care agents are administered in compositions, i.e. they may be administered together (i.e., simultaneously), but may also be administered separately or sequentially. In general, combination therapy is typically administered together, the rationale being that such simultaneous administration induces multiple simultaneous stresses on the virus. The specific dosages given will depend on absorption, inactivation and excretion rate of the drugs as well as other factors. It is to be noted that dosage values will also vary with the severity of the condition to be alleviated. The terms "co-administration" or "combined administration" or "administered in combination with" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present disclosure. The administration of a pharmaceutical combination of the disclosure results in a beneficial effect, e.g. a synergistic or additive therapeutic effect, compared to a monotherapy applying only one of its pharmaceutically active ingredients or as compared to the current standard of care therapy. The treatment used in the methods described herein may be administered by any conventional route. One or more components may be administered parentally, e.g., in the form of injectable solutions or suspensions, or in the form of injectable deposit formulations. Preferably, the non-immunosuppressive cyclophilin inhibitor, in particular alisporivir and/or NIM811 will be administered orally in the form of capsules, tablets or solutions or suspensions for drinking. Pharmaceutical compositions for oral administration comprising alisporivir and/or NIM811 typically further comprise one or more pharmaceutically acceptable carrier substances. Typically, these compositions are concentrated and need to be combined with an appropriate diluent, e.g., water, prior to administration. Pharmaceutical compositions for parenteral administration typically also include one or more excipients. Optional excipients include an isotonic agent, a buffer or other pH-controlling agent, and a preservative. These excipients may be added for maintenance of the composition and for the attainment of preferred ranges of pH (about 6.5-7.5) and osmolarity (about 300 mosm/L).

The administration of alisporivir or NIM811 as described herein is in a single dose form or in more than one dosage form; one or more oral dosage forms may be administered at each time per day. In some embodiments, alisporivir and/or NIM811 is administered in doses of 200 mg to 1000 mg.

The efficacy of the therapy regimen may be monitored using standard protocols. Treatment may be followed by determinations of Coronavirus levels in serum. For example, the patients may be assessed for the presence of Coronavirus RNA in their serum.

The following Examples illustrate the invention described herein.

EXAMPLES

Example 1

Antibodies and Drugs

Mouse antibody 1H11 (1:20,000) recognizing HCoV-NL63 N-protein was obtained from INGENASA, Spain (Sastre, P., Dijkman, R., Camunas, A., Ruiz, T., Jebbink, M. F., van der Hoek, L., Vela, C., Rueda, P., 2011. Differentiation between human coronaviruses NL63 and 229E using a novel double-antibody sandwich enzyme-linked immunosorbent assay based on specific monoclonal antibodies. Clin Vaccine Immunol 18(1), 113-118). Anti-Lamin A (1:20,000) was purchased from Biomol, Hamburg, Germany. Goat-anti-Lamin B (1:400), rabbit anti-CypA (1:2,000) and rabbit anti-CypB (1:1,000) were obtained from Santa Cruz Biotechnology, Enzo Life Sciences and Abcam, respectively. Secondary antibodies were received from Dianova (goat anti-rabbit-Ig-horse radish peroxidase HRP, [1:3,000] and rabbit-anti-goat-Ig-HRP [1:3,000]) and Sigma (anti-mouse-Ig-HRP [1:40,000]).

Compounds 1, 2, 3, 4, and 5 were synthesized as previously described (Malesevic, M., Gutknecht, D., Prell, E., Klein, C., Schumann, M., Nowak, R. A., Simon, J. C., Schiene-Fischer, C., Saalbach, A., 2013. Anti-inflammatory Effects of Extracellular Cyclosporins Are Exclusively Mediated by CD147. J Med Chem 56(18), 7302-7311; Prell, E., Kahlert, V., Rucknagel, K. P., Malesevic, M., Fischer, G., 2013. Fine tuning the inhibition profile of cyclosporine A by derivatization of the MeBmt residue. Chembiochem 14(1), 63-65). The synthesis of 6 will be described elsewhere. Alisporivir and NIM811 were provided by Novartis (Switzerland). CsA, CsD and FK506 were obtained from Sigma-Aldrich, Santa Cruz (Germany) and Enzo Life Sciences (Germany), respectively.

NFAT Reporter Gene Assay

The tests were performed as described (Prell et al., 2013). Briefly, Jurkat cells were transfected with NFAT reporter gene plasmid and incubated with 0.5 µM inhibitor or 0.5% DMSO (control) for 30 min. Ca2+ mobilization was initiated by phorbol 12-myristate 13-acetate/ionomycin or tumor necrosis factor-α and cultured for additional 5 h before harvesting and determining luciferase activity in cell lysates. NFAT activities are expressed as mean SD of triplicates in three independent experiments.

NFAT-GFP Nuclear Translocation Assay

HeLa cells were cultured in Dulbecco's Modified Eagle Medium (DMEM) containing 10% FBS and 1% penicillin/streptomycin. NFAT3-GFP plasmid was transfected into HeLa cells by using Lipofectamine LTX and Plus Reagent (Life Technologies) when the cells were 70% confluent. Subsequently, drugs were added to the medium at a final concentration of 40 nM. 19 hours later, ionomycin was added at a final concentration of 2 µM to induce NFAT3-GFP translocation. Pictures were taken using a fluorescence microscope (Leica DM4000 B) 10 minutes after ionomycin induction.

RNA Isolation and Real-Time Reverse Transcription-PCR (RT-PCR)

CaCo2 cells were infected with HCoV-NL63 at MOI=0.004 for one hour. After removal of virus inoculum and two PBS washes, fresh medium supplemented with increasing inhibitor concentrations was added. After 48 hours RNA was extracted from 10 µl culture supernatant using the High Pure Viral Nucleic Acid Kit (Roche) and eluted in 13 µl. Quantification was done by real-time PCR SensiFAST Probe Hi-ROX One-Step kit (Bioline GmbH, Germany) allowing reverse transcription, cDNA synthesis and PCR amplification in a single step. Samples were analysed by ABI Prism 7000 Cycler I Sequencing Detection System. A standard curve was produced using serial dilutions of viral RNA of HCoV-NL63 virus stock with known virus titer.

PCR primers (Herzog, P., Drosten, C., Muller, M. A., 2008. Plaque assay for human coronavirus NL63 using human colon carcinoma cells. Virol J 5, 138) used were NL-63RF2 for 5'-CTTCTGGTGACGCTAGTACAGCTTAT-3' (SEQ ID NO: 1)(genome position nt 14459-14484) and NL-63RR2rev 5'-AGACGTCGTTGTAGATCCCTAACAT-3'(SEQ ID NO: 2)((genome position nt 14573-14597) and NL-63 probe was 5'-FAMCAGGTTGCTTAGTGTCCCATCAGATTCAT-TAMRA-3' (SEQ ID NO: 3) (genome position nt 14532-14560).

Western Blotting

To determine N-protein expression in the presence of inhibitors Caco-2 cells were infected at virus MOI=0.004 for one hour in six-well plates. Virus was washed off with PBS and inhibitors were added to the medium at the respective concentrations. After 48 hrs cells were harvested and lysed with 1% NP-40 in 50 mM Tris-HCl, pH 7.5, 150 mM NaCl, 10 mM DTT and Protease Inhibitor Cocktail (Hoffmann La Roche) 250 µl lysis buffer. Proteins were separated by 8 or 12.5% SDS-PAGE and electroblotted onto nitrocellulose membranes. Latter were blocked with 5% milk powder in TBST buffer. Incubation with primary antibodies was usually carried out at 4° C. overnight. Secondary antibody incubation was performed at room temperature for two hours. After each incubation step, membranes were washed three times with TBST for 10 min. HRP was developed with Immobilon Western blot HRP chemiluminiscent substrate from Milipore. Membranes were exposed to X-ray film (Agfa).

Cyclophilin Knockdown Cell Lines.

Cyclophilin knockdown cell lines were generated using shRNA expression vectors (Sirion GmbH, Martinsried, Germany) as recently described for FKBP1A/B (Carbajo-Lozoya, J., Muller, M. A., Kallies, S., Thiel, V., Drosten, C., von Brunn, A., 2012. Replication of human coronaviruses SARS-CoV, HCoV-NL63 and HCoV-229E is inhibited by the drug FK506. Virus Res 165(1), 112-117). Briefly, cells were transduced at MOI 30 with MISSION™ lentiviral non-target control gene, PPIA from a target set SHVRS-NM_021130 (TRCN000049232) and PPIB from a target set SHVRSNM_000942 (TRCN0000049251). Stably shRNA-expressing cells were generated through 3 weeks of bulk-selection in 10-15 µg/ml puromycin-containing medium (DMEM+10% FCS+2 mM L-glutamine+1 mM Na-pyruvate).

TABLE 1

| A) shRNA sequences used for lentiviral-based gene knockdown | | |
|---|---|---|
| Particle set | Target | shRNA sequence (5'->3') |
| Non-target control TRC1.5 Vector (pLKO.1-puro) | | CCGGCAACAAGATGAAGAGCACCAACTCGAGTTGGTGCTCTTCAT CTTGTTGTTTTTG (SEQ ID NO: 4) |

TABLE 1-continued

| | | |
|---|---|---|
| PPIA: SHVRS-<br>NM_021130 | TRCN000<br>049232 | CCGGGTTCCTGCTTTCACAGAATTACTCGAGTAATTCTGTGAAAG<br>CAGGAACTTTTG (SEQ ID NO: 5) |
| PPIB: SHVRS-<br>NM_000942 | TRCN000<br>049251 | CCGGGTTCTTCATCACGACAGTCAACTCGAGTTGACTGTCGTGAT<br>GAAGAACTTTTG (SEQ ID NO: 6) |

B) Sequences of primers used for quantification of gene knockdown

| qRT-PCR primer | sequence (5'->3') |
|---|---|
| hPPIA_F | CAGACAAGGTCCCAAAGACAG (SEQ ID NO: 7) |
| hPPIA_R | TTGCCATCCAACCACTCAGTC (SEQ ID NO: 8) |
| hPPIB_F | CTCTCCGAACGCAACATGAAG (SEQ ID NO: 9) |
| hPPIB_R | ACCTTGACGGTGACTTTGGG (SEQ ID NO: 10) |

Investigation of Antiviral Activities of Cyclophilin Inhibitors, in Particular DEB025 (Alisporivir) and NIM811, on Coronavirus Characterization of Non-Immunosuppressive CsA- and FK506-Derivatives First, CsA analogues were isolated in 1977 from *Trichoderma polysporum* Traber, R., Kuhn, M., Loosli, H. R., Pache, W., von Wartburg, A., 1977. [New cyclopeptides from *Trichoderma polysporum* (Link ex Pers.) Rifai: cyclosporins B, D and E (author's transl)]. Helv Chim Acta 60(5), 1568-1578). CsD was described in 1993 as a weak immunosuppressant in lymphocyte proliferation assays with about 10% of the CsA activity (Sadeg, N., Pham-Huy, C., Rucay, P., Righenzi, S., Halle-Pannenko, O., Claude, J. R., Bismuth, H., Duc, H. T., 1993a. In vitro and in vivo comparative studies on immunosuppressive properties of cyclosporines A, C, D and metabolites M1, M17 and M21. Immunopharmacol Immunotoxicol 15(2-3), 163-177; Sadeg, N., Pham Huy, C., Martin, C., Warnet, J. M., Claude, J. R., 1993b. Effect of cyclosporin A and its metabolites and analogs on lipid peroxidation in rabbit renal microsomes. Drug Chem Toxicol 16(2), 165-174). In CsD a valine is located at position 2 instead of L-a-aminobutyric acid. The two prominent CsA derivatives NIM811 (contains a methyl-isoleucine at position 4 instead of the methyl-leucine) and Alisporivir (contains a methyl-alanine at position 3 instead of sarcosine and an N-ethyl valine at position 4, instead of N-methyl leucine) were intensively tested in clinical trials as anti-HIV-1 and anti-HCV drugs (Fischer, G., Gallay, P., Hopkins, S., 2010. Cyclophilin inhibitors for the treatment of HCV infection. Curr Opin Investig Drugs 11(8), 911-918; Gallay, P. A., Lin, K., 2013. Profile of alisporivir and its potential in the treatment of hepatitis C. Drug design, development and therapy 7, 105-115; Lin, K., Gallay, P., 2013. Curing a viral infection by targeting the host: the example of cyclophilin inhibitors. Antiviral research 99(1), 68-77; Membreno, F. E., Espinales, J. C., Lawitz, E. J., 2013. Cyclophilin inhibitors for hepatitis C therapy. Clinics in liver disease 17(1), 129-139; Vermehren, J., Sarrazin, C., 2011. New HCV therapies on the horizon. Clin Microbiol Infect 17(2), 122-134).

A further set of CsA analogues was developed, fine-tuned by derivatization at MeBmt residue 1 of CsA and a FK506 derivative with different properties regarding the inhibition of drug-Cyp/FKBP complexes, CaN phosphatase-, NFAT activities (FIG. 1, Table 2). Synthesis of drug derivatives compounds 1 and 2 were previously described (Prell, E., Kahlert, V., Rucknagel, K. P., Malesevic, M., Fischer, G., 2013. Fine tuning the inhibition profile of cyclosporine A by derivatization of the MeBmt residue. Chembiochem 14(1), 63-65). The CsA derivatives 3, 4, 5 were synthesized as published (Malesevic, M., Gutknecht, D., Prell, E., Klein, C., Schumann, M., Nowak, R. A., Simon, J. C., Schiene-Fischer, C., Saalbach, A., 2013. Anti-inflammatory Effects of Extracellular Cyclosporins Are Exclusively Mediated by CD147. J Med Chem 56(18), 7302-7311). The chemical synthesis of the non-immunosuppressive FK506 analogue 6 starting from the parent drug FK506 will be published elsewhere.

TABLE 2

Properties of CsA (compounds 1-5) and FK506 (compound 6) analogues with respect to inhibition of PPIA in a protease-coupled PPIase assay, CaN, NFAT, and NFAT-GFP nuclear translocation. Methods are described in (Prell et al., 2013). The last column represents the EC50 inhibitory values of the peptides on HCoV-NL63 infection of Caco-2 cells.

| Name | In vitro inhibition human CypA $IC_{50}$ [nM] | In vitro inhibition CnA $IC_{50}$ [µM] | In vitro inhibition NFAT reporter gene assay $IC_{50}$ [µM] | NFAT-GFP translocation in HEK-293 cells | Inhibition of HCoV-NL63 in CaCo-2 $EC_{50}$ [µM] |
|---|---|---|---|---|---|
| CsA | 9.1 +/− 0.8 | 0.05 | 1.6 ± 0.3 nM | no | 0.9-2.0 |
| CsD | nd | nd | nd | no | 2.5 |
| ALV | nd | nd | nd | yes | 0.8 |
| NIM811 | nd | nd | nd | yes | 0.8 |
| 1 | 9.1 +/− 1.4 | no | no | yes | 1.6 |
| 2 | 57.5 +/− 6.9 | no | no | yes | 7.9 |
| 3 | 11.9 +/− 0.9 | 6.9 | 45% at 10 µM | yes | 1.1 |
| 4 | 14.1 +/− 1.9 | ~10 | 1.3 | yes | 8.1 |
| 5 | 16.6 +/− 2.3 | >10 | 1.2 | yes | 2.3 |
| FK506 | nd | nd | nd | no | 6.6 |
| 6 | 10.2 +/− 1.9 | no | no | yes | 4.2 |

These PPIase inhibitors were biochemically characterized by determining their inhibitory potency in a standard PPIase assay. Inhibition of the CaN phosphatase, the influence on cell-based NFAT reporter gene activity and NFAT translocation by the drugs (Table 2) were performed using published procedures (Pfefferle, S., Schopf, J., Kogl, M., Friedel, C. C., Muller, M. A., Carbajo-Lozoya, J., Stellberger, T., von Dall'Armi, E., Herzog, P., Kallies, S., Niemeyer, D., Ditt, V., Kuri, T., Zust, R., Pumpor, K., Hilgenfeld, R., Schwarz, F., Zimmer, R., Steffen, I., Weber, F., Thiel, V., Herrler, G., Thiel, H. J., Schwegmann-Wessels, C., Pohlmann, S., Haas, J., Drosten, C., von Brunn, A., 2011. The SARS-coronavirus-host interactome: identification of cyclophilins as target for pan-coronavirus inhibitors. PLoS Pathog 7(10), e1002331; Prell, E., Kahlert, V., Rucknagel, K. P., Malesevic, M., Fischer, G., 2013. Fine tuning the inhibition profile of cyclosporine A by derivatization of the MeBmt residue. Chembiochem 14(1), 63-65).

While the $IC_{50}$ values for PPIase inhibition were similar to that of CsA, compound 2 (57.5+/−6.9 nM) showed a higher $IC_{50}$ value indicating lower binding affinity, but inhibition was still found in the low nanomolar range. CnA activity could not be inhibited at all by binary PPIase/drug complexes of 1, 2, 6. In contrast, CnA activity was weakly inhibited at very high concentrations of the drug/CypA complexes as indicated by $IC_{50}$ values in the range of 10 μM for compounds 3 ($IC_{50}$ 6.9 μM), 4 ($IC_{50}$~10 μM) and 5 ($IC_{50}$>10 μM)). In addition, these derivatives also demonstrated low ability ($IC_{50}$ 10 μM, 1.3 μM and 1.2 μM, respectively), compared with CsA ($IC_{50}$ 1.6 nM), to reduce the NFAT-driven reporter gene expression in a luciferase-coupled NFAT reporter gene assay indicating a greatly diminished immunosuppressive activity in a cellular assay. Although, peptides 4 and 5 showed higher CnA inhibition in vitro NFAT inhibition was remarkable indicating a gain of CaN effects in vivo. The 45% NFAT inhibitory activity at 10 μM of 3 still represents a 5000 fold lower influence of the CsA derivative on NFAT-regulated signaling pathways as compared to CsA.

Figure 2:
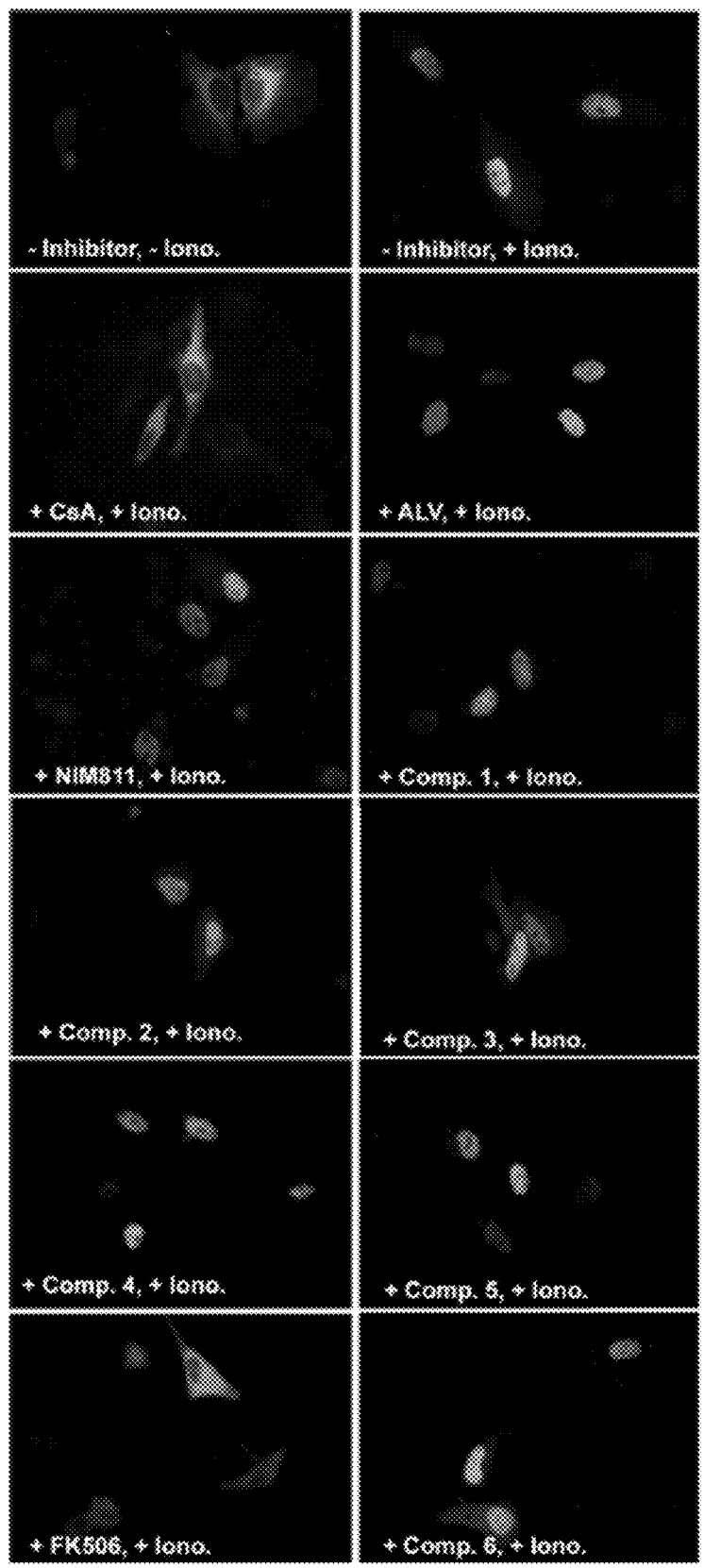
FIG. 2 depicts the effect of CsA, FK506 and derivatives on NFAT-GFP nuclear translocation as a measure of immunosuppressive activity. NFAT3-GFP expression plasmid was transfected into HeLa cells. Subsequently, inhibitor compounds (comp.) were added to the medium at a final concentration of 40 nM. 19 hours later, ionomycin was added at a final concentration of 2 μM to induce NFAT3-GFP translocation. Pictures were taken 10 minutes after Ionomycin (Iono.) induction. CsD showed the same behavior as CsA.

The drug derivatives were further characterized by a NFAT-GFP nuclear translocation assay. HEK293 cells were transfected with a plasmid encoding a NFAT-GFP fusion construct under the control of the CMV promoter (FIG. 2). Upon $Ca^{2+}$ mobilization by ionomycin the cellular phosphatase CaN dehosphorylates the NFAT transcription factor which is subsequently translocated to the nucleus. The Cyp-binding immunosuppressants CsA, CsD and the FKBP-binding FK506 induce the binding as protein complexes to CaN thus inactivating its phosphatase activity. As a result NFAT is not transferred to the nucleus. Complexes of the modified drugs 1-6 with both types of PPIases, i.e. Cyp/modified CsA or FKBP/modified FK506 derivative complexes, have a greatly reduced potency to inhibit CaN and thus might allow the translocation of NFAT to the nucleus and the transcriptional regulation of immune genes. Consequently, ALV, NIM811 and the whole series of newly synthesized drug derivatives 1-6 clearly allow NFAT-GFP translocation to the nucleus and can be thus considered as non-immunosuppressive under these assay conditions (Table 2). In conclusion, in three different assays all synthetic drug derivatives proved to be inert or nearly inert in the suppression of the cellular immune response at an almost unchanged binding and inhibitory potency against the PPIase activity of the respective drug receptor.

Non-Immunosuppressive CsA- and FK506-Derivatives Inhibit Replication of HCoV-NL63

Figure 3A:
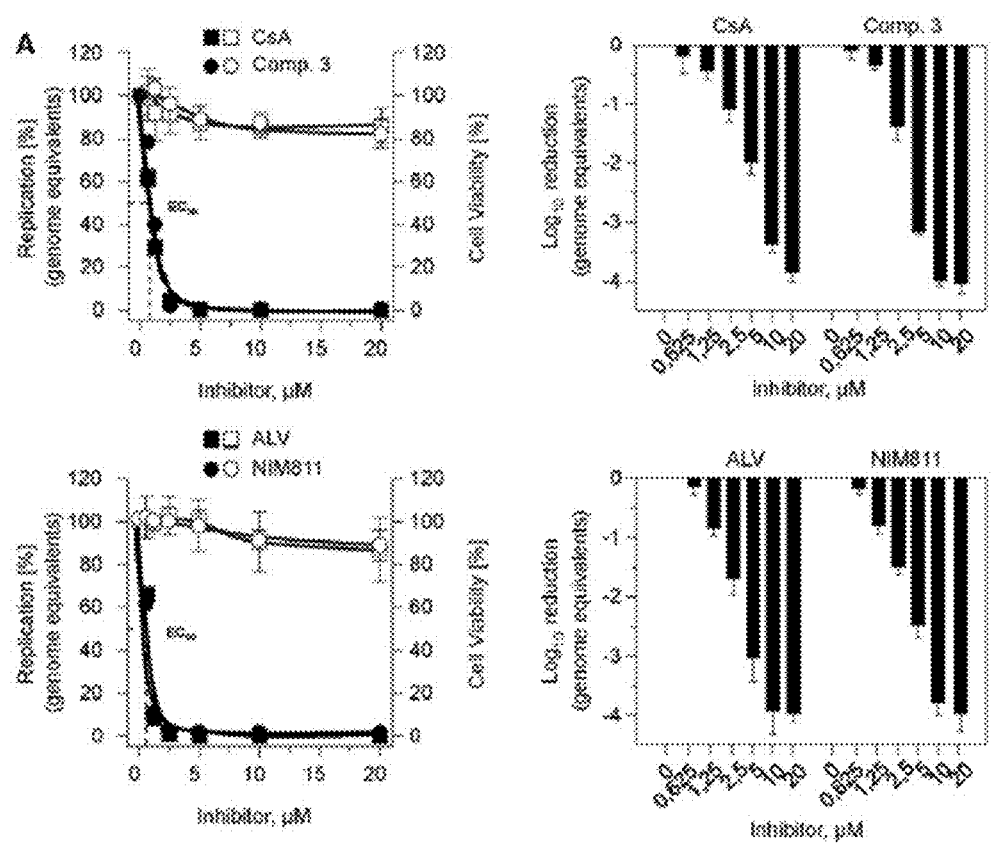
FIGS. 3A-B depict the effect of CsA and FK506 derivatives on HCoV-NL63 replication in Caco-2 cells. Genome equivalents were determined by qPCR and cell viabilities by Cell Titer Glow kit (Promega). Data shown are mean values of a representative experiment performed in at least triplicates. Left Y-axes represent the percentage of reduction of virus replication in linear scale (left panel column) and in log scale (right panel column). Right Y-axes indicate the percentage of the cell viabilities. X-axes indicate increasing inhibitor concentrations at which virus replication was determined. Closed/open squares and closed/open circles represent the reduction of genome equivalents and cell viability at the indicated inhibitor concentrations (X-axes), respectively.
Figure 3B:
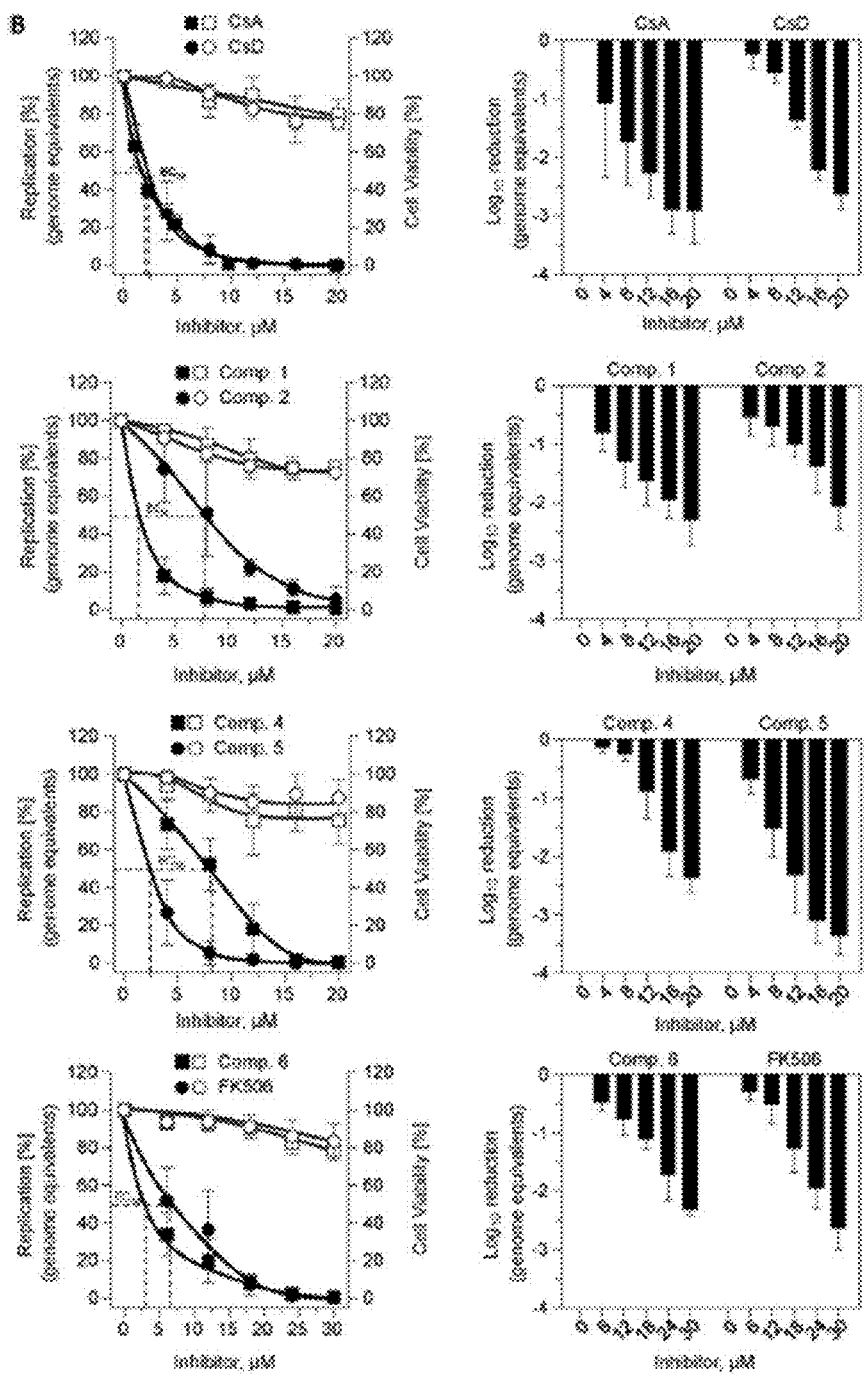

To examine the inhibitory effects of the described non-immunosuppressive CsA and FK506 derivatives on the replication of HCoV-NL63, Caco-2 cells were infected with HCoV-NL63 as described (Carbajo-Lozoya, J., Muller, M. A., Kallies, S., Thiel, V., Drosten, C., von Brunn, A., 2012. Replication of human coronaviruses SARS-CoV, HCoV-NL63 and HCoV-229E is inhibited by the drug FK506. Virus Res 165(1), 112-117). FIG. 3 shows the effects of CsA and seven non-immunosuppressive derivatives (ALV, NIM811, 1, 2, 3, 4, 5) and of FK506 and its descendant 6 on HCoV-NL63 replication in Caco-2 cells. Left panels represent the percentage reduction of virus replication (left Y-axes) and cell viabilities (right Y-axes). The right panels indicate the respective log 10 titer reduction. The graphs were plotted using Prism 5 (GraphPad Software, Inc.) and by a non-linear regression with a variable slope algorithm, the curve was fitted for each respective inhibitor and the $EC_{50}$ calculated. The figure shows two independent sets of experiments (see FIGS. 3A, 3B) carried out at different times. When performing individual virus inhibition experiments CsA was always included as an internal control. Minor variations are explained by the use of different compound batches. FIG. 3A summarizes results obtained with peptides CsA, 3, ALV and NIM811. FIG. 3B delineates results with peptides CsD, 1, 2, 4, 5, and of FK506 and 6. The combination of the two peptides in each individual graph was chosen arbitrarily. Only FK506 and its derivative 6 were grouped together as they belong to the same compound family.

From the inhibition curves it can be concluded that all peptides tested, i.e. CsA, CsD and FK506 as well as ALV, NIM811 and the new derivatives, clearly inhibit the replication of HCoV-NL63 in Caco-2 cells at low micromolar concentration levels. The $EC_{50}$ inhibitory scores (Table 2) reside in a range between 0.8 and 8.1 μM with ALV/NIM811 and 4 showing the lowest and highest concentrations, respectively. 1, 3 acted similarly. Also, the FK506 derivative behaved very similar to its ancestor molecule. There was no clear correlation of the inhibitory effect to in vitro inhibition of CypA, CnA or NFAT activity.

Effects of Inhibitory Drugs on HCoV-NL63 N Protein Expression

Figure 4:
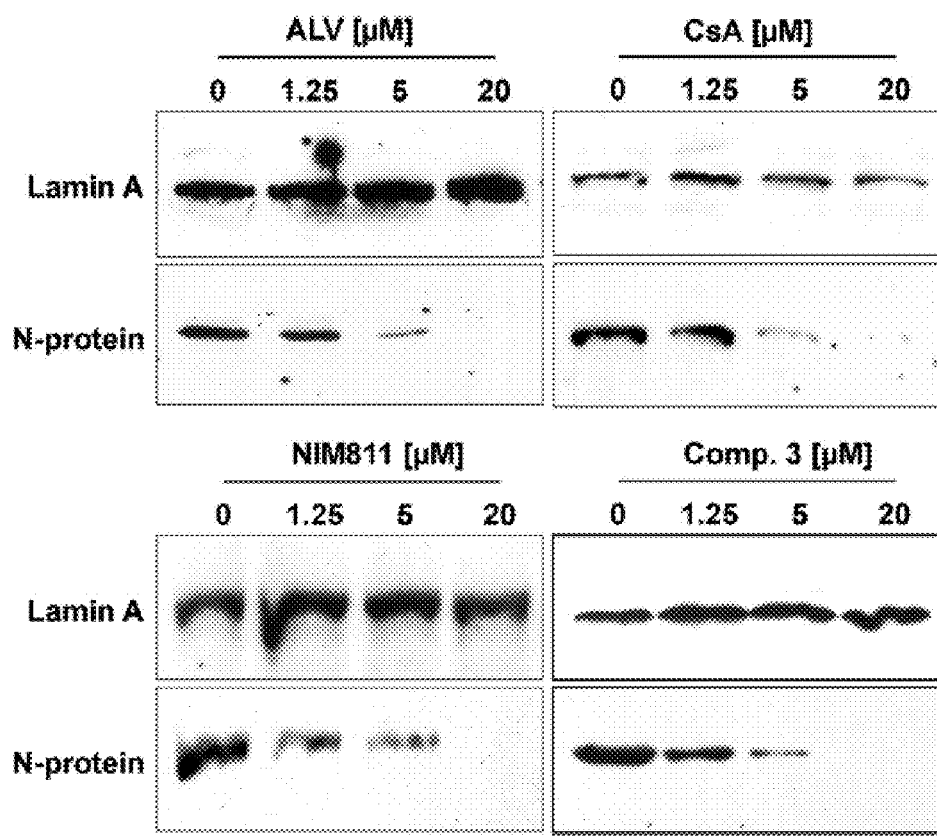
FIG. 4 depicts Western blot analysis of N protein expression in HCoV-NL63-infected CaCo2 cells upon treatment with increasing concentrations of CsA, ALV, NIM811 and compound 3. N-Protein was detected with a mouse mab against N-protein. A rabbit anti-Lamin A antibody was used to detect Lamin A as a loading control.

To study the effect of CsA, ALV, NIM-811 and substance 3 on viral protein expression, cells were incubated with concentrations of 0 to 20 μM of the respective inhibitors for 48 hours. Western blot analysis of HCoV-NL63-infected CaCo2 cells was performed utilizing an anti-N-protein antibody. FIG. 4 clearly shows a significant decrease of the N-protein between 1.25 μM and 5 μM. It is not detectable any more at 20 μM of the respective inhibitor. This suggests that the drugs inhibit an important step in the viral replicative cycle.

HCoV-NL63 Replication Depends on Cyclophilin a

In order to examine whether cellular CypA or CypB, encoded by the PPIA and PPIB genes, respectively, are required for HCoV-NL63 replication, Cyclophilin Caco-2 knockdown cell lines were established using lentiviral shRNA expression vectors as recently described for FKBP1A/B (Carbajo-Lozoya, J., Muller, M. A., Kallies, S., Thiel, V., Drosten, C., von Brunn, A., 2012. Replication of human coronaviruses SARS-CoV, HCoV-NL63 and HCoV-229E is inhibited by the drug FK506. Virus Res 165(1), 112-117). Rather high puromycin concentrations (10-15 μg/ml) were needed for selection as Caco-2 cells are very efficiently depleted from inhibitory drug molecules because of enhanced expression of multi drug resistant protein 1 gene (Takara, K., Tsujimoto, M., Ohnishi, N., Yokoyama, T., 2002. Digoxin up-regulates MDR1 in human colon carcinoma Caco-2 cells. Biochem Biophys Res Commun 292(1), 190-194). mRNA expression was quantified initially from bulk-selected knockdown and control cells by real-time RT-PCR. For reverse transcription, 1 µg of total RNA was used. Amplification products were detected by SYBR I, and amplicon integrity was verified by melting point analysis. Human topoisomerase 1 gene (hTOP1) served as a reference gene for non-target control, PPIA and PPIB to determine the specificity of the knockdown. mRNA expression levels of PPIA and PPIB were then determined by real-time RT-PCR. In case of PPIA, the knockdown in the puromycin bulk-selected Caco-2 cells was incomplete as determined by Western blot (about 79%) and qPCR analysis. Here virus growth was detectable by qPCR. We reasoned that these cells were not appropriate for testing the effect of CypA on virus replication. As CypA comprises 0.1-0.4% of total cytosolic protein of most eukaryotic tissues (Harding, M. W., Handschumacher, R. E., Speicher, D. W., 1986. Isolation and amino acid sequence of cyclophilin. J Biol Chem 261(18), 8547-8555) individual cell clones were selected from the Caco-2-PPIA bulk KD cells by limited dilution in the presence of puromycin and checked for knockdown quality.

Individual clones were expanded and tested for expression by Western blot and qPCR (FIG. 5). FIG. 5A shows Western blot analyses of the PPIA KD clone (polyclonal rabbit anti-CypA) used for further infection experiments. The CypB KD was demonstrated (FIG. 5A) using a polyclonal rabbit anti-CypB antibody. For control the housekeeping gene Lamin B was probed with a polyclonal goat anti-Lamin B antibody. As Lamin B levels showed no differences in Caco-2 wt, Caco-2sh control and both knockdown cells, CypA was barely detectable while CypB was completely reduced. By qPCR comparison to non-target controls the CypA and CypB knockdown cell lines were determined to be 97% and 98%, respectively (FIG. 5B).

FIG. 5C shows an infection of Caco-2 wt, Caco-2sh control, Caco-2-PPIA KD and Caco-2-PPIB KD cells with serial dilutions of HCoV-NL63 virus inoculum. The plaque titration assay (FIG. 5C) clearly indicates comparable virus titers (FIG. 5D) in both control and in the Caco-2-PPIB-KD cell lines. The virus did not grow in the Caco-2-PPIA KD cells at all indicating the dependence of virus replication on CypA. Similar results were obtained by qPCR (not shown).

The main goal of the study was to test and compare the inhibitory effect of the chemically difficult-to-synthesize cyclosporines ALV and NIM811 with a set of drug derivatives 1-5 which result from the chemically well-tractable side chain in position 1 of CsA. In addition, the FK506 derivative 6 should provide a first indication of feasibility of expanding the concept of antiviral non-immunosuppressive CypA inhibitors into the field of FKBP inhibitors. Data on the inhibition of HCoV-NL63 replication were compared with the immunosuppressive immunophilin binders CsA, CsD and FK506. All derivatives inhibit the PPIase activity of their respective binding proteins thus preventing their catalytic function in assisting client proteins to fold correctly. When compared with already known non-immunosuppressive drugs, the new compounds were not only more easily accessible by chemical synthesis but also showed a favorable ratio of PPIase inhibition to cellular toxicity. All compounds were tested in an NFAT-GFP nuclear translocation assay (FIG. 2). Upon mobilization of $Ca^{2+}$ by ionomycin, NFAT-GFP remained in the cytoplasm in the presence of CsA, CsD and FK506. This indicates that the CypA/CsA, CypA/CsD or FKBP/FK506 complexes inactivate the CnA phosphatase thus preventing NFAT dephosphorylation and nuclear translocation which constitutes the basis for immunosuppression. For CsD it is clear that it exerts a rather strong immunosuppressive activity as opposed to earlier reports ascribing only about 10% of the CsA activity to the molecule (Sadeg, N., Pham-Huy, C., Rucay, P., Righenzi, S., Halle-Pannenko, O., Claude, J. R., Bismuth, H., Duc, H. T., 1993a. In vitro and in vivo comparative studies on immunosuppressive properties of cyclosporines A, C, D and metabolites M1, M17 and M21. Immunopharmacol Immunotoxicol 15(2-3), 163-177). In the presence of ALV, NIM811 and all the newly synthesized drug derivatives 1 to 6, NFAT migrated to the nucleus within minutes confirming their non-immunosuppressive activity. The new set of drugs was also characterized in vitro with respect to inhibition of CypA in a protease-coupled PPIase assay, CnA and NFAT assay and cell permeability. The potency of PPIase inhibition was comparable to CsA. Only in the case of compound 2 it was increased by about sixfold. The $IC_{50}$ values of CnA inhibition was achieved for CsA at 0.05 µM whereas for three of the new compounds 138-fold to 200-fold higher concentrations were needed.

Virus inhibition experiments (FIG. 3, Table 2) clearly showed the highly effective inhibition of HCoV-NL63 by ALV ($EC_{50}$: 0.8 µM) and NIM811 ($EC_{50}$: 0.8 µM) which closely resembles the patterns of CsA ($EC_{50}$: 0.9-2.0 µM) and CsD ($EC_{50}$: 2.5 µM). The $EC_{50}$ values of the CsA derivatives range between 1.1 µM and 8.1 µM. $EC_{50}$ values of FK506 and its derivative 6 were 6.6 µM and 4.2 µM, respectively. Taken together, all the derivatives inhibited virus replication in the low micromolar range similar to our previous report on the inhibition of various human and animal CoVs with CsA (Pfefferle, S., Schopf, J., Kogl, M., Friedel, C. C., Muller, M. A., Carbajo-Lozoya, J., Stellberger, T., von Dall'Armi, E., Herzog, P., Kallies, S., Niemeyer, D., Ditt, V., Kuri, T., Zust, R., Pumpor, K., Hilgenfeld, R., Schwarz, F., Zimmer, R., Steffen, I., Weber, F., Thiel, V., Healer, G., Thiel, H. J., Schwegmann-Wessels, C., Pohlmann, S., Haas, J., Drosten, C., von Brunn, A., 2011. The SARS-coronavirus-host interactome: identification of cyclophilins as target for pan-coronavirus inhibitors. PLoS Pathog 7(10), e1002331).

The HCoV-NL63-N protein plays a crucial role in the viral life cycle. It was analyzed as a representative of viral protein expression in the presence of increasing concentrations of CsA, ALV, NIM-811 and substance 3. The protein decreased at 1.25 µM and it was not detectable any more at concentrations above 5 µM. Thus, there is a clear inhibitory effect of the different peptides on N protein expression and virus replication. Whether inhibition is a result of lacking cyclophilin interaction with Nsp1 or another viral protein cannot be decided at the current stage. As the N protein of SARS-CoV was reported to bind to CypA (Luo, C., Luo, H., Zheng, S., Gui, C., Yue, L., Yu, C., Sun, T., He, P., Chen, J., Shen, J., Luo, X., Li, Y., Liu, H., Bai, D., Yang, Y., Li, F., Zuo, J., Hilgenfeld, R., Pei, G., Chen, K., Shen, X., Jiang, H., 2004. Nucleocapsid protein of SARS coronavirus tightly binds to human cyclophilin A. Biochem. Biophys. Res. Commun. 321(3), 557-565) and CypA is incorporated into SARS-CoV particles (Neuman, B. W., Joseph, J. S., Saikatendu, K. S., Serrano, P., Chatterjee, A., Johnson, M. A., Liao, L., Klaus, J. P., Yates, J. R., III, Wuthrich, K., Stevens, R. C., Buchmeier, M. J., Kuhn, P., 2008. Proteomics analysis unravels the functional repertoire of coronavirus nonstructural protein 3 2. J. Virol. 82(11), 5279-5294.) the inhibitors might also act directly on CypA/N-protein complexes, if these also exist in HCoV-NL63. It can also not be ruled out that further viral proteins require CypA functions.

An important question was whether CypA is the crucial cyclophilin required for CoV replication. For HCV there were some discrepancies on the necessity of CypA and CypB virus growth. Recent studies demonstrate that CypA is the key host factor for HCV replication (Baugh, J., Gallay, P., 2012. Cyclophilin involvement in the replication of hepatitis C virus and other viruses. Biological chemistry 393(7), 579-587; Kaul, A., Stauffer, S., Berger, C., Pertel, T., Schmitt, J., Kallis, S., Zayas Lopez, M., Lohmann, V., Luban, J., Bartenschlager, R., 2009. Essential Role of Cyclophilin A for Hepatitis C Virus Replication and Virus Production and Possible Link to Polyprotein Cleavage Kinetics. PLoS Pathog 5(8), e1000546). In order to address the role of the two members of the Cyp family for HCoV-NL63 replication, CaCo2 cell lines were developed with individual knockdowns for CypA and CypB on a lentiviral basis (FIG. 5). The characterization at protein (5A) and RNA (5B) levels indicated efficient KD of the two Cyps. In plaque titration experiments performed on CaCo2 wt, CaCo2sh (non-target) and CaCo2ΔCypB the virus grew at comparable titers (5C, 5D). In contrast, CaCo2ΔCypA cells did not support virus growth at all indicating the dependence on functional CypA.

Regarding Cyp requirement for CoV replication, contradictory results were reported by de Wilde et al (2011). While previous CoV data on CsA inhibition (Schöpf, J., Pfefferle, S., Kögl, M., Herzog, P., Müller, M. A., Kallies, S., D. Muth, D., T. Kuri, T., Ebel, F., Friedel, C., Zimmer, R., Weber, F., Haas, J., Thiel, H.-J., Herder, G., Schwegmannn-Wessels, C., Thiel, V., Drosten, C., von Brunn, A., 7-11 Apr. 2010. Applying systems biology to Severe Acute Respiratory Coronavirus and its human host: identification of a cellular target and its inhibitor for antiviral intervention. 4th European Congress of Virology, Cernobbio, Lake Como, Italy) were basically confirmed, the report claims that neither CypA nor CypB are required for replication of SARS-CoV and Mouse Hepatitis Virus (MHV) on the basis of siRNA PPIA and PPIB knockdown experiments. However, both siRNA knockdowns were rather incomplete in terms of the residual CypA or CypB protein level leaving enough PPIase activity in the infected cells to support viral replication. At least for HCoV-NL63, it was demonstrated that in lentivirally produced knockdown cells CypA but not CypB is the required molecule. Interestingly, showing a similarly poor knockdown of PPIA the same authors claim in a follow-up study on arteriviruses that PPIA is the required cyclophilin for nidovirus replication (de Wilde, A. H., Li, Y., van der Meer, Y., Vuagniaux, G., Lysek, R., Fang, Y., Snijder, E. J., van Hemert, M. J., 2013. Cyclophilin inhibitors block arterivirus replication by interfering with viral RNA synthesis. Journal of virology 87(3), 1454-1464). Coronaviridae and Arteriviridae are both families within the order of Nidovirales. They are both positive-stranded with similar genome organization and genome length of 27 to 32 kb and 13 to 16 kb, respectively, and they share a number of enzymatic functions. Since both families are sensitive to CsA the involvement of cyclophilins in nidovirus replication as a general principle is reasonable.

From the HCoV-NL63 infectivity studies in Caco-2-PPIA/PPIB KD cells, it was found that that the most abundant CypA of the viral host is a prerequisite of CoV replication. The interaction of SARS-CoV Nsp1 in Y2H and in mammalian protein-binding assays with several cyclophilin isoforms suggests the potential involvement of additional cyclophilins in the infection process. It has to be examined systematically whether CypA and further cyclophilins bind to other viral proteins. Furthermore, knowledge about the regulatory role of the catalytic activity of the PPIase subfamilies of cyclophilins and FK506-binding proteins, both of which were shown here to be critical in the viral replication process requires identification of their protein substrates in the coronaviral background.

The four non-SARS-related HCoVs (HCoV-OC43/229E/NL63 and /HKU1) are major causes of relatively mild respiratory tract infections in immunocompetent hosts. However, clinical manifestations like bronchiolitis and pneumonia can be severe especially in young children, the elderly and immunocompromised patients (van der Hoek, L., 2007. Human coronaviruses: what do they cause? Antivir Ther 12(4 Pt B), 651-658). Infection occurs in early childhood and the detection of anti-S IgG antibodies in >70% of the general human population demonstrates their high prevalence (Zhou, W., Wang, W., Wang, H., Lu, R., Tan, W., 2013. First infection by all four non-severe acute respiratory syndrome human coronaviruses takes place during childhood. BMC infectious diseases 13, 433). Furthermore, the zoonotic transmission potential of HCoV-NL63 (Huynh, J., Li, S., Yount, B., Smith, A., Sturges, L., Olsen, J. C., Nagel, J., Johnson, J. B., Agnihothram, S., Gates, J. E., Frieman, M. B., Baric, R. S., Donaldson, E. F., 2012. Evidence supporting a zoonotic origin of human coronavirus strain NL63. Journal of virology 86(23), 12816-12825) and of the highly aggressive SARS-CoV and MERS-CoV (Gallagher, T., Perlman, S., 2013. Public health: Broad reception for coronavirus. Nature 495(7440), 176-177) demand the development of effective drugs preventing or alleviating virus growth and pathogenicity.

The marked inhibition of HCoV-NL63 replication by the non-immunosuppressive derivatives of CsA and of FK506 highlights the functional relevance of host cell cyclophilins and FKBPs as antiviral targets.

Replication of human pathogenic coronaviruses can be inhibited in vitro by cyclosporin A, a well-known immunosuppressive drug which binds to cellular cyclophilins thus inactivating their cis-trans peptidyl-prolyl isomerase function. Here we tested the effect of non-immunosuppressive Cyclosporin A derivatives and of non-synonymous single nucleotide polymorphisms in the PPIA gene, encoding Cyclophilin A, on Human Coronavirus-229E replication. Cyclosporin A derivatives Alisporivir, NIM811, compound 3 as well as control molecules were used to assess their inhibitory potential for HCoV-229E-GFP and -Luciferase viruses in cultured Huh-7.5 cells. Virus growth was also analysed in Huh-7.5 cells carrying a knockdown or mutations in Cyclophilin A using small hairpin RNAs. HCoV-229E-GFP replicated in various human hepatoma Huh-7-derived cell lines. As shown by luciferase measurement and Western blot analysis of the viral N protein HCoV-229E-LUC replication was effectively inhibited in Huh-7.5 at 18 and 48 hour timepoints by all non-immunosuppressive Cyclosporin A derivatives tested with EC50s at low micromolar ranges. Both viruses expressing GFP or luciferase required Cyclophilin A expression as shown by PPIA knockdown (Huh-7.5KD-PPIA). In three Huh-7.5-CypA SNP mutants (D66E, N106I, G96D) luciferase expression was reduced to levels similar to the cyclophilin A knockdown, whereas in mutants Huh-7.5-CypA (E134K, E84D, I89T) expression levels were more similar to the reconstituted Huh-7.5-CypA-KD+wtCypA-constructs. Thus, HCoV-229E, replication depends on functional and correctly folded CypA and is effectively inhibited by non-immunosuppressive CsA derivatives suggesting them as possible candidates for the treatment of HCoV infection.

Coronaviruses (CoVs) infect a variety of mammalian species including bats, mice, cats, birds and humans causing infection of respiratory and gastrointestinal tract and the central nervous system (1). The six human CoVs, namely HCoV-229E, -OC43, -NL63, -HKU1, SARS (severe acute respiratory syndrome)-CoV, MERS (Middle East respiratory syndrome)-CoV, mainly target the respiratory tract. Whereas 229E and OC43 are known since the mid-1960s SARS-CoV appeared first in China causing a worldwide outbreak with 8,098 cases and 774 deaths in 2002/03 and with enormous socio-economic impact. Arising interest in CoVs led to the discovery of NL63 in 2004 and HKU1 in 2005. MERS was identified in 2012 in Saudi Arabia with 536 laboratory confirmed cases of human infections and 145 deaths (WHO Global Alert and Response 9 May 2014). 15 to 30% of common colds are caused by HCoVs (229E, OC43, NL63, HKU1) with mostly seasonal occurrence. They usually infect the upper respiratory tract. However, during occasional spread to the lower respiratory tract they account for significant hospitalizations of young children, the elderly and immunocompromised individuals. A recent study on NL63 and 229E seroconversion in children showed that 75% and 65% in the age group 2.5 to 3.5 years were NL63 and 229E seropositive, respectively, indicating that seroconversion occurs before the age of 3.5 years. In a further epidemiological study 207 (14%) out of 1471 hospitalized children (<2 years) were HCoV-positive. A large-scale survey on 11,661 respiratory samples diagnosed 267 (2.3%) positive for at least one CoV corresponding to 8.15% of virus detections. 11% to 41% CoVs were found in multiply infected samples, e.g. with RSV. Primary targets of CoV infection are airway epithelial cells. Other cell types can be infected in vitro. 229E infects and replicates in neural cells, hepatocytes, monocytes and macrophages. It has massive cytopathic effects on and kills dendritic cells (DCs) but not monocytes 7. DCs are antigen-presenting cells and play a major role as links between innate and adaptive immunity. Their death at an early stage of 229E infection might contribute to the failure of the establishment of long-lasting immunity, since the virus can re-infect the same host multiple times. Until now no effective drug treatment is available neither against the common cold nor the highly pathogenic CoVs. Great efforts have been made to discover anti-MERS agents by screening defined drug libraries. A nsp13 helicase inhibitor prevents replication of SARS-/MERS-CoVs and MHV. Screening 16,671 diverse compounds for anti-229E activity Lundin et al. have identified an inhibitor (K22) specifically targeting membrane-bound coronaviral RNA synthesis at an early step of viral replication. In order to identify host-targeting agents (HTAs) we have recently performed virus-host protein-protein interaction screenings by testing individual SARS-CoV ORFS against human cDNA libraries utilizing high-throughput yeast-2-hybrid techniques. In this study we had identified cyclophilins and FK506-binding (FKBPs) proteins as cellular interaction partners of the viral Nsp1 protein and the cyclophilin-binding immunosuppressive drug cyclosporin A (CsA) as a replication inhibitor of the various human and animal CoVs including SARS-CoV, NL63 and 229E. In a follow-up study we found that non-immunosuppressive CsA derivatives Alisporivir (ALV), NIM811 and further compounds inhibit replication of NL63 and that CypA is an essential cellular molecule required for virus replication. Similar inhibitory properties of CsA and derivatives on CoV and Arterivirus replication, both belonging to the order of Nidovirales were described. Here we demonstrate the inhibitory effects of non-immunosuppressive CsA derivatives on 229E replication in various Huh-7-derived hepatoma cell lines, the requirement of CypA in Huh-7.5 cells and the effect of individual single nucleotide polymorphism mutations (SNPs) on virus propagation.

Example 2

Antibodies and Drugs

Mouse antibody 1H11 (1:20,000) recognizing HCoV-229E N-protein was obtained from INGENASA, Spain (24). Anti-Lamin A (1:20,000) was purchased from Biomol, Hamburg, Germany. Secondary antibodies were received from Biomol (goat anti-rabbit-Ig-horse radish peroxidase HRP, [1:3000] and rabbit-anti-goat-Ig-HRP [1:3000]) and Sigma Aldrich (anti-mouse-Ig-HRP [1:40,000]). Alisporivir (formerly DEB025) and NIM811 were provided by Novartis (Basel, Switzerland). CsA and Rapamycin (RAPA) were obtained from Sigma-Aldrich (Germany). Cyclosporin H (CsH) was synthesized according to published procedures (25). Synthesis of compound 3 was described recently (20, 26).

Viruses

Human hepatocellular carcinoma cells Huh-7, Huh-7.5 cells (27) and subclones were maintained in Dulbecco's modified Eagle medium (Invitrogen, Karlsruhe, Germany) supplemented with 10% fetal bovine serum, L-glutamine, non-essential amino acids, penicillin, and streptomycin. Cells harboring small hairpin RNA (shRNA) constructs were kept in the presence of blasticidin (5 µg/mL). Cells harboring pWPI-encoded CypA variants were additionally kept in the presence of G418 (750 µg/mL). The Huh-7.5/CypA variant cell lines used in this study (Huh-7.5KD-PPIA/Huh-7.5sh non-target control/Huh-7.5-CypA-KD+wtCypA/Huh-7.5-CypA SNP mutants (D66E, N106I, G96D, E134K, E84D, I89T) were described recently (28). Huh-7D (29) and Huh-7 Lunet (30) cells were published. Cell viabilities were determined by Cell Titer Glow kit (Promega).

HCoV-229E viruses expressing Renilla luciferase (LUC) (Pfefferle et al., 2011) or Green Fluorescent Protein (GFP) (31, 32) reporter genes were used to examine the inhibitory effect of compounds. Generally, Huh-7.5 cells were infected with MOI=0.1 and incubated for two days in the presence of increasing concentrations of inhibitor in the culture medium. Viral replication was determined by measuring Renilla luciferase activity or GFP fluorescence using a Leica DMI 4000B microscope.

Western Blotting

N-protein expression in the presence of inhibitors or in Huh-7.5 CypA variants was analysed as described recently. Briefly, Huh-7.5 cells were infected at HCoV-229E-LUC/-GFP virus MOI=0.1 for one hour in six-well plates. Virus was washed off with PBS and inhibitors were added to the medium at the respective concentrations. After 48 hrs cells were harvested and lysed with 250 µl lysis buffer (1% NP 40 in 50 mM Tris HCl, pH 7.5, 150 mM NaCl, 10 mM DTT and Protease Inhibitor Cocktail [Hoffmann La Roche]). Proteins were separated by 8 or 12.5% SDS-PAGE and electroblotted onto nitrocellulose membranes. Latter were blocked with 5% milk powder in TBST buffer. Incubation with primary antibodies was usually carried out at 40 C overnight. Secondary antibody incubation was performed at room temperature for two hours. After each incubation step membranes were washed three times with TBST for 10 min. HRP was developed with Immobilon Western blot HRP chemiluminiscent substrate from Milipore. Membranes were exposed to X-ray film (Agfa).

Coding Non-Synonymous PPIA Gene SNPs

SNPs used in Huh-7.5 PPIA manipulated cell lines: Rs61747111 (D66E), rs17850166 (N106I), rs17850033 (I89T), rs11547706 (G96D), rs1059983 (E84D), rs9769523 (E134K) (28) The results are shown in the following.

HCoV229E Grows in Different Huh-7-Derived Cell Lines

Human hepatocellular carcinoma cells (Huh-7) support the replication of a number of viruses including HCV (33), HCoV-229E, SARS-CoV and MERS-CoV (34). A number of Huh-7 mutant cell lines [Huh-7.5 (27), Huh-7D (29), Huh-7 Lunet (35)] were generated in order to increase Hepatitis C Virus (HCV) permissiveness for viral and replicon propagation. For instance, Huh-7.5 cells carry a mutation in the cytosolic retinoic acid-inducible gene I (RIG-I) which is a pattern recognition receptor for triggering type I interferon pathways by sensing HCV dsRNA. Huh-7D carries mutations outside of the RIG-I coding region.

In order to test the permissiveness of the hepatoma cell line for HCoV-229E replication we infected the different cell lines with HCoV-229E-GFP. All cell lines were permissive to infection at similar extends. Although infection of Huh-7.5 was slightly less effective we chose to primarily work with this cell line as there were CypA mutants available (28).

HCoV-229E Replication is Inhibited by Non-Immunosuppressive CsA Derivatives

We have recently reported on the biochemical and immunological characteristics and on the inhibitory effect of a number of CsA-derived compounds on the replication of HCoV-NL63 (20). The molecules included CsA, ALV, NIM811, as well as newly developed CsA position 1-modified compound 3. Here we tested the inhibitory effect on the replication of HCoV-229E using recombinant viruses expressing Renilla luciferase (229E-LUC) or GFP (229E-GFP). FIG. 1 shows replication in Huh-7.5 cells reflected by Renilla luciferase activity of 229E-LUC at 18 and 48 hrs p.I. and the corresponding $EC_{50}$ (effective inhibitory concentration) values (Table 3).

TABLE 3

$EC_{50}$ values for the individual inhibitors determined at 18 and 48 hrs p.I. Values were calculated by a non-linear regression with a variable slope algorithm and fitted curves for each respective inhibitor.

| $EC_{50}$ p.I (hours) | µM 18 | µM 48 |
| --- | --- | --- |
| ALV | 2.77 | 1.37 |
| NIM | 3.11 | 1.19 |
| CsA | 2.09 | 0.97 |
| CsH | — | — |
| FK506 | 2.96 | 0.86 |
| RAPA | — | — |
| Comp. 3 | 2.05 | 0.92 |

Figure 6A:
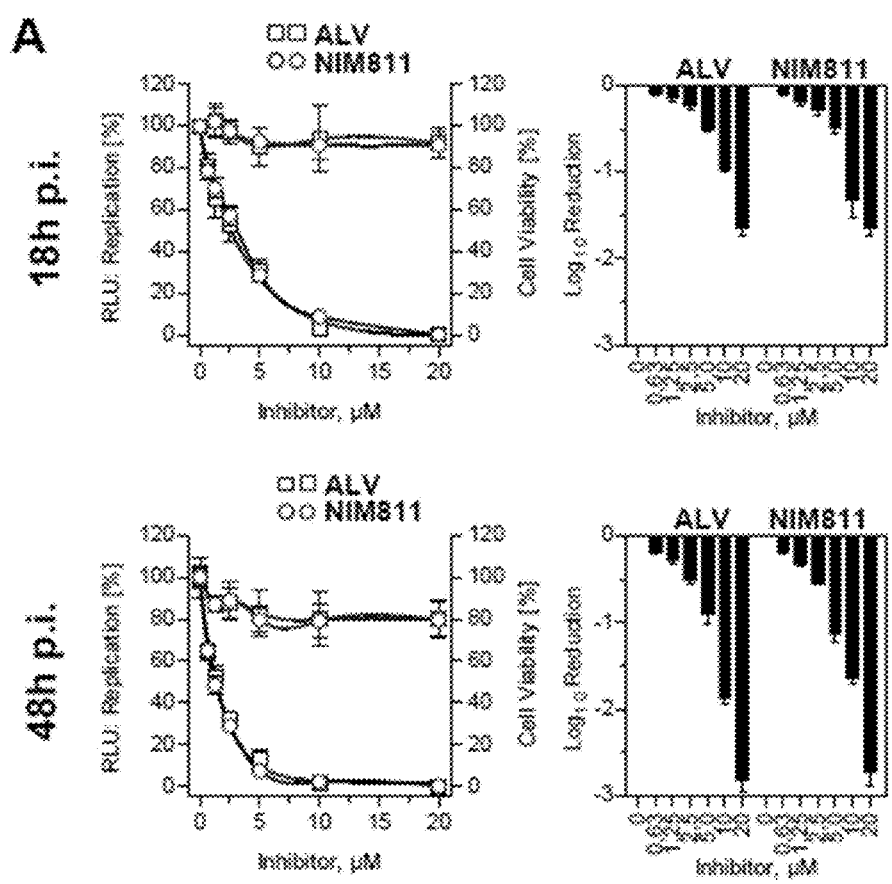
FIGS. 6A-C show the effect of CsA and various non-immunosuppressive derivatives on HCoV-229E-LUC (MOI=0.1) replication in Huh-7.5 cells determined by Renilla luciferase activity measurement. Left Y-axes represent the percentage of reduction of virus replication in linear (left panels) or in log scale (right panels) at the indicated inhibitor concentrations given on the X-axis. Cell viability with mock-treated cells set to 100% are shown on the right Y-axes of the left panels. Measurements were taken 18 and 48 hrs p.i. CsH and RADA served as controls. The graphs were plotted using Prism 5 (GraphPad Software, Inc.) and by a non-linear regression with a variable slope algorithm, the curve was fitted for each respective inhibitor and the $EC_{50}$ was calculated.
Figure 6B:
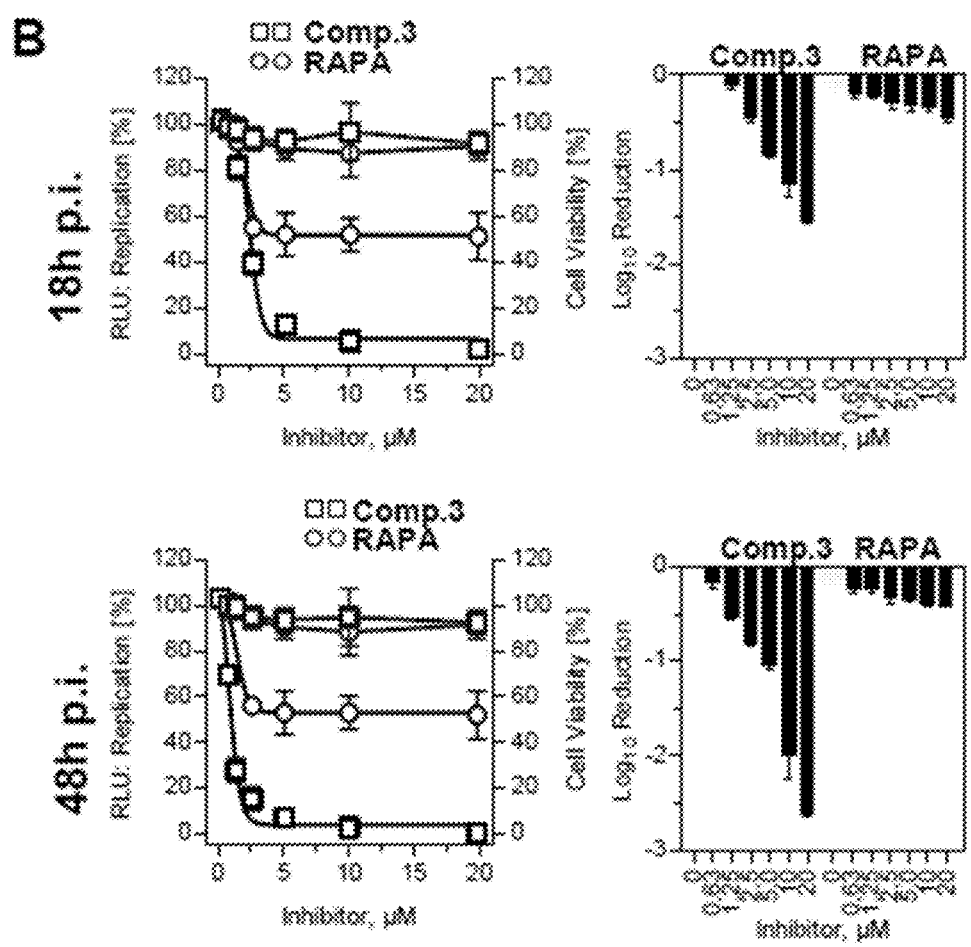
Figure 6C:
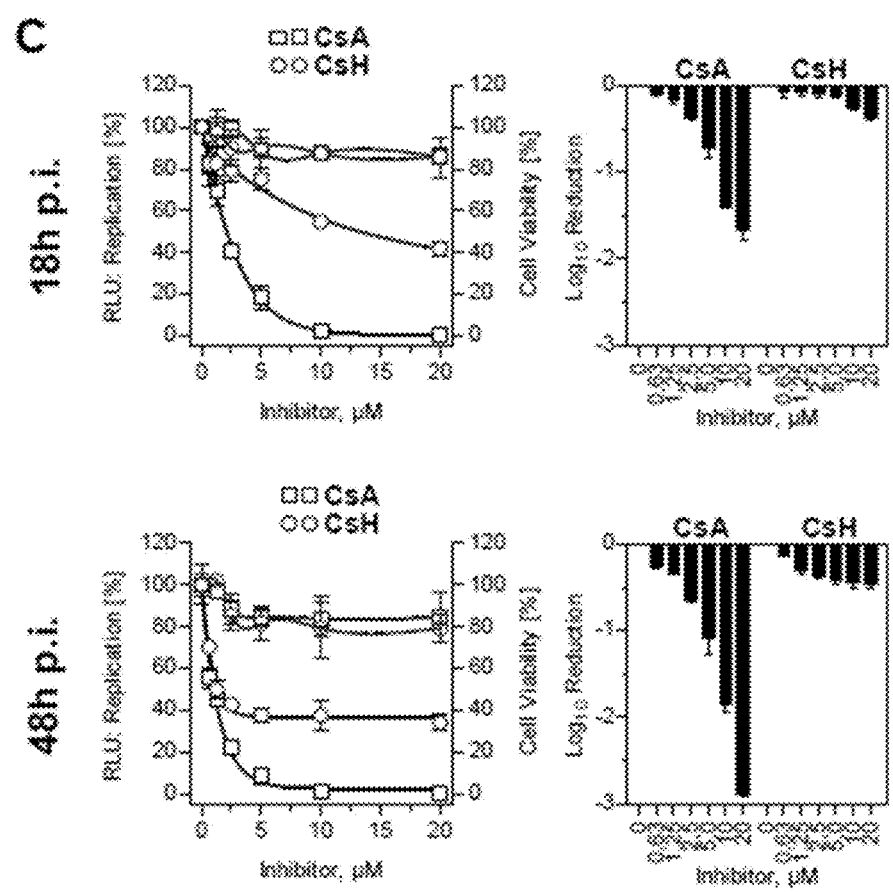

It is clearly demonstrated that similarly to CsA the non-immunosuppressive molecules ALV, NIM811 (FIG. 6A), compounds 3 (FIG. 6B) inhibit 229E-LUC replication in the low micromolar range. Cell viability was only slightly affected at highest concentrations used. As controls we included CsH and Rapamycin. CsH is a stereoisomer of CsA in which D-methylvaline at position 11 substitutes the natural L-methylvaline. Following the minor affinity for CypA this substitution abrogates the immunosuppressive and anti-inflammatory properties of CsA (36, 37). It should thus not inhibit viral replication. FIG. 1C shows a slight residual inhibitory activity of the CsH preparation. We explain this as a result of traces of CsA-like impurities present in the CsH preparation. Due to the chemical similarity of these molecules it is very difficult to remove them from the product batches. Also very low inhibition of CypA in the PPIase assay could be observed with this compound. The FKBP-binding drug FK506 was included as a positive control of inhibition, which is the consequence of blocking the PPIase activity of FKBPs. We had shown earlier that also FK506 inhibits 229E and NL63 replication in vitro (32). The immunosuppressive drug rapamycin was used as a control molecule to test the effect of immunosuppressants on CoV replication. It also binds to FKBP1A (=FKBP12), but as opposed to FK506 it interferes with the mTOR (mechanistic Target of Rapamycin) pathway by inhibiting a serine/threonine protein kinases (38). FIG. 6B shows only some minor background inhibitory activity of rapamycin as compared to FK506. Thus, the lack of effective inhibition of viral replication by CsH and rapamycin which both do not affect the PPIAse activities of cyclophilins strongly argue for the requirement of this function for coronavirus replication.

Effects of Inhibitory Drugs on HCoV-229E N Protein Expression

Figure 7:
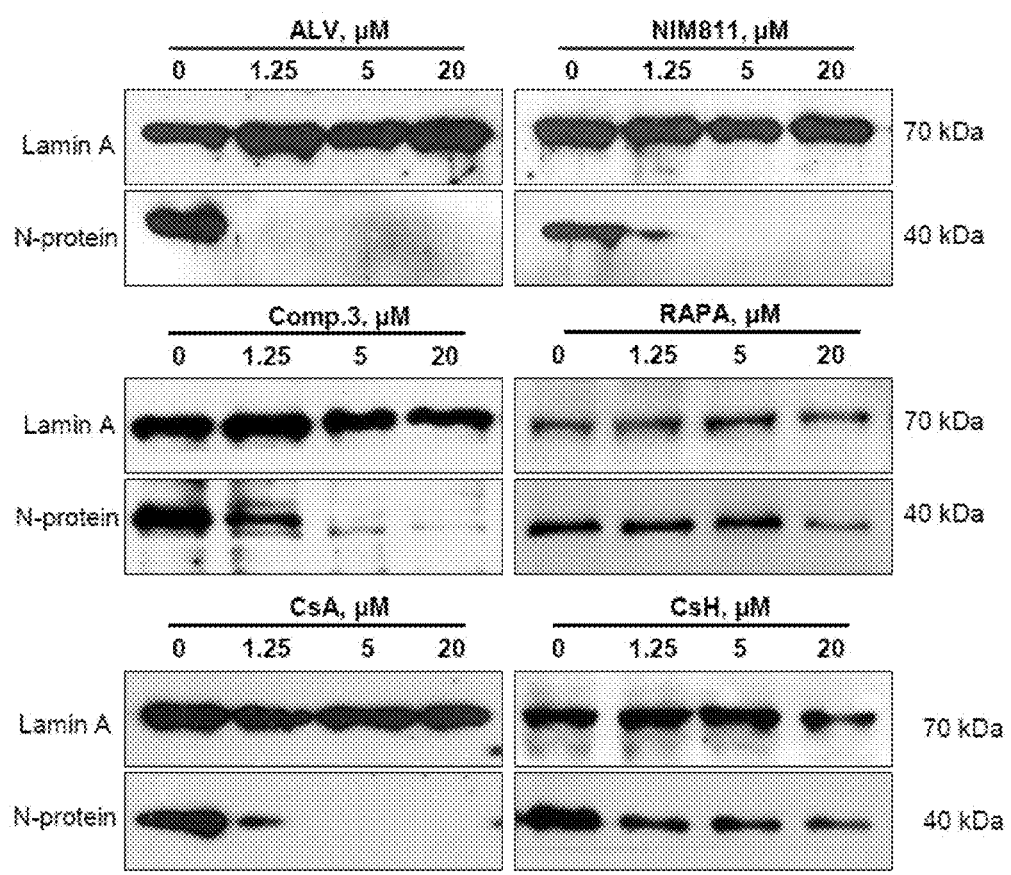
FIG. 7 is a Western blot analysis of N protein expression in HCoV-229E-LUC-infected Huh-7.5 cells. Cells were treated for 48 hrs with increasing concentrations of ALV, NIM811, compound 3, RAPA, CsA and CsH and then processed for WB analysis. As a measure of viral replication N-Protein was detected with a mouse mab against N. A rabbit anti-Lamin A antibody was used to detect Lamin A as a loading control.

The N protein is required for virus replication and for the propagation of replicons. Its primary function is to encapsidate and to protect genomic RNA. Lack of N protein is thus a measure of lacking viral replication. To study the effect of CsA, ALV, NIM-811 and compound 3 on viral N protein expression Huh-7.5 cells were incubated with concentrations of 0 to 20 µM of the respective inhibitors for 48 h. Western blot analysis of NL63-infected CaCo-2 cells was performed utilizing an anti-N antibody. FIG. 7 demonstrates the decrease of the N protein between 1.25 µM and 5 µM in the presence of ALV, NIM811 compound 3. In case of ALV N protein is not detectable anymore at 1.25 µM. Similarly, presence of the positive control CsA also decreases N protein expression between 1.25 and 5 µM whereas CsH and rapamycin allow significant N protein synthesis even at 20 µM. It is not clear whether the inhibitors act on the N protein itself, on other viral proteins or both. However, viral N protein essential for replication is not synthesized in the presence of the inhibitors.

HCoV-229E Replication Depends on Cyclophilin A

Figure 8C:
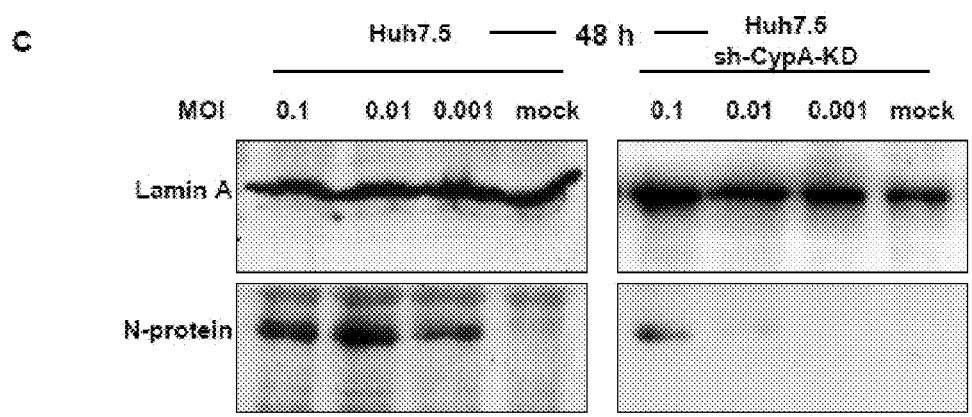

For HCoV-NL63 we have recently shown that replication in CaCo2 cells depends on cyclophilin A (CypA) but not CypB. As HCoV-229E does not replicate in this cell line we could not use the respective KD cells for testing its cyclophilin requirement. We therefore utilized Huh-7.5 CypA knockdown cells constructed for the analysis of Hepatitis C virus (28). FIG. 8 shows the growth behavior of 229E-GFP on Huh-7.5 cells at three different virus concentrations (0.1, 0.01, 0.001 MOI) 24 and 48 hrs p.I. Green cells are virus-infected. As judged by overall GFP fluorescence inspection the virus increasingly spreads in Huh-7.5 cells during the observed time-line. Cell nuclei are shown in blue by DAPI staining. The number of infected cells decreases with decreasing MOI (FIG. 8A). In Huh-7.5sh-KD-PPIA cells only a small number of infected cells can be observed at MOI 0.1, but not at MOI 0.01 anymore. Representative areas of the fixed microscopic slides are shown. Western blot analysis of viral N protein after two days of infection clearly demonstrates much lower protein levels in the knockdown cell line at MOI 0.1 and 0.01 as compared to Huh-7.5 cells (FIG. 8C). Lamin A was used as a loading control. The low levels of GFP fluorescence and N protein expression in Huh-7.5KD-PPIA can be explained by incomplete knockdown of CypA leaving enough molecules which can promote virus replication at very low levels.

Coding Non-Synonymous SNP Variants in the PPIA Gene Limit HCoV-229E Replication

For HCV, viral growth behavior was shown to depend on protein stability of the individual SNP variants. Although mRNA levels determined by qPCR analysis were comparable in Huh-7.5 wt and CypA variants protein levels of D66E were reduced and G96D and N106I appeared near absent (28). For the infection experiments with HCoV-229E we analysed relative CypA mRNA expression levels in the various cell lines by qPCR in relation to the house keeping gene hTOP1 with the level in Huh-7.5 set to 1.0 (FIG. 9A). CypA mRNA levels in the non-target control (sh-Ctr) and in the D66E, G96D, E134K and I89T variants were slightly decreased. Levels in E84D and in the wtCypA-reconstituted Huh-7.5PPIA-KD (sh-CypA-KD) cells were increased. In Huh-7.5KD-PPIA (sh-CypA-KD) cells PPIA mRNA was close to background confirming that the knockdown was very efficient although not complete. In order to assess growth properties of HCoV-229E-LUC the various cell lines were infected with 0.1 MOI of the virus and grown for 24 and 48 h (FIG. 9B). As judged by Luciferase protein expression levels (RLU) virus grew best in Huh-7.5 cells with an about two-fold increase over the sh-CypA-KD+wt-CypA and the non-target sh-Ctr cells. In sh-CypA-KD cells 259 virus replication was decreased by factors of 10 and 20 at 24 h and 48 h timepoints, respectively. In case of the E134K, E84D and I89T mutant virus growth was slightly decreased as compared to the sh-CypA-KD+wt-CypA and the sh-Ctr cells. Very interestingly, in D66E, N106I and G96D, 229E replication was almost completely abolished as it was in the case of sh-CypA-KD cells. To assess viral replication at the level of essential N protein production in HCoV-229E-LUC virus-infected cells (MOI 0.01) Western blot analysis of viral N protein two days p.I. was performed (FIG. 9C). N protein levels were similar in Huh-7.5, sh-Ctr and sh-CypA-KD+wt-267 CypA reconstituted cells. In sh-CypA-KD cells N was almost absent confirming the 268 requirement of CypA for HCoV-229E replication.

Outbreaks of the highly pathogenic and in many cases lethal SARS-CoV in 2002/03 and of MERS-CoV in 2012 put pressure on the development of ideally broad-acting antiviral drugs to the commonly underestimated Coronaviridae virus family. This is even more desirable as most of the human CoVs are of zoonotic origin and have crossed species barriers from bat [SARS (39), NL63 (40), 229E (41)], cattle [OC43 (42)], or cameloids [MERS (43, 44)] to humans. In a recent study we had identified CsA as a broad-spectrum inhibitor of CoV replication in humans, mouse, cat, pig and bird with cyclophilins as a probable cellular targets (19). De Wilde et al. extended this list to MERS-CoV (22) and arteriviruses equine arteritis virus (EAV) and porcine reproductive and respiratory syndrome virus (PRRSV) (45) indicating the broad activity on the two families Coronaviridae and Arteriviridae of the order of Nidovirales. Cyclophilins are ubiquitous enzymes catalyzing the cis/trans isomerization of prolyl peptide bonds thus facilitating protein folding (46). The most prominent human cyclophilin is CypA with important roles in many biological processes such as protein folding, trafficking and T-cell activation (47). Latter function is prevented by the coincidental binding of the CsA/CypA complex to the cellular phosphatase calcineurin (CaN). One of the functions of this enzyme is, upon Ca2+ intracellular release, to dephosphorylate the NFAT (Nuclear Factor of Activated T-cells) transcription factor, which can then translocate to the nucleus and exert its transcriptional functions on immune gene promoters. Immunosuppression is the consequence of the lack of NFAT translocation. The second effect of CsA/CypA binding is the inactivation of the PPIase activity preventing correct folding of cellular, and in the case of a number of virus infections of viral proteins including Human Immunodeficiency Virus 1 (HIV-1) and hepatitis C virus (HCV) (48). Thus, cyclophilins are discussed as therapeutic targets of viral liver diseases (49). Of course, for treatment of virus infection the inhibition of activity of cyclophilins but not the immunosuppressive activity of CsA is desirable. A number of CsA derivatives have been developed which do fulfill these criteria: ALV (50), NIM811 (51), SCY-635 (52), Sangliferins (53) and a series of new compounds described recently (20, 26, 54). Alisporivir has experienced substantial clinical testing and safety database development with more than 2000 patients treated for up to 48 weeks. NIM811 or SCY-635 have been administered in a very small number (<50 patients) only in short proof-of-concept trials. Compound 3 or sanglifehrins have not been given to patients yet. We have shown the successful inhibition of HCoV-NL63 replication by ALV, NIM811 and position 1-modified CsA derivatives (20) and the requirement of CypA, not CypB for NL63 replication. Here we demonstrate the inhibition of HCoV-229E by the same compounds as well as the presence and correct folding of CypA as prerequisite of virus replication. We first tested the growth behavior of 229E in human hepatoma cell lines Huh-7, Huh-7.5, Huh-7D and Huh-7-Lunet. The various cell clones were originally generated by different groups to increase permissiveness of HCV replication. At MOI 0.1 all four cell lines were easily infected with HCoV-229E-GFP virus. Although growth efficiency was best in Huh-7D cells we chose to continue most experiments in the Huh-7.5 cell line as von Hahn et al. had recently described hepatocytes expressing CypA variants that are resistant to HCV infection and replication (28). We used these cell lines to characterize the behavior of 229E replication upon CypA-depletion and mutational modification. Virus inhibition experiments (FIG. 6, Table 3) clearly demonstrate the highly effective inhibition of the Renilla luciferase-expressing 229E-LUC with decreasing $EC_{50}$ values between 18 and 48 hours p I Inhibition patterns of ALV, NIM811 (both FIG. 6A), compounds 3 (FIG. 6B) and CsA (FIG. 6C) look very similar with $EC_{so}$ values of 1.37, 1.19, 0.97 and 0.92 μM, respectively. Log titer reductions range between 2.5 and 3 at the 48 h time point. Cell viabilities decreased only slightly at the highest drug concentrations (20 μM) used. In general, CoV inhibition seems to require low micromolar ranges of CsA and its non-immunosuppressive derivatives which was recently found by us (19, 20) and by others (23).

Interestingly, inhibition of HCV with ALV and CsA/NIM811 is commonly observed at low and high nanomolar concentrations, respectively, unraveling ALV as the most effective compound. Currently, we cannot explain why the CypA inhibitors (especially ALV) are much more potent on preventing HCV than CoV replication, or why their inhibitory activity on CoVs is rather similar. One explanation might be that several CoV proteins depend on the activity of CypA and/or have higher affinities to coronaviral as compared to HCV proteins thus requiring higher inhibitor doses to abolish interactions. CsH and rapamycin were used as negative control compounds. Both allow the transfer of NFAT to the nucleus. CsH does not bind to CypA. Thus, no CsH/CypA complexes exist that can bind to and inactivate CaN. Rapamycin 330 targets FKBPs similarly to the immunosuppressant FK506. In an earlier report we had 331 described 229E inhibition by the FKBP-binding drug FK506 (32). However, the rapamycin/FKBP complexes inhibit the unrelated m-TOR pathway in contrast to FK506/FKBP complexes which bind similar to the CsA/Cyp complexes to CaN thus inactivating the CaN phosphatase activity and as a consequence the NFAT pathway. Both compounds do not inhibit 229E replication. The minor reduction observed in the case of CsH we attribute to traces of CsA, from which CsH was synthesized and which can only be separated quantitatively by enormous experimental expenditure. The reason why rapamycin as opposed to FK506 does not inhibit 229E replication is not clear. It is not known whether all FKBP proteins are inhibited by rapamycin. Also, the sub-cellular localization of rapamycin and FK506 might be different. The inhibitory effect of the different substances is further supported by the expression analysis of the 229E N protein. N is required for virus replication and thus essential for the viral life cycle.

Western blot analysis (FIG. 7) demonstrates the lack of N protein expression during 229E-LUC infection of Huh-7.5 cells at ALV, NIM811, Compound 3 and CsA inhibitor concentrations above 1.25 µM and 5 µM, respectively, but not for CsH and rapamycin. CsA and its non-immunosuppressive derivatives inhibit replication of a number of viruses including HCV and HIV-1. In most cases the responsible cyclophilin is CypA (55). For HCoV-NL63 we have recently shown that CypA expression is essential in CaCo-2 cells (20). Here we examined whether this is also the case for 229E propagation. We utilized a series of Huh-7.5 CypA mutant cell lines, which were originally constructed for the study of the requirement of stable CypA for HCV replication (28). On the basis of six coding non-synonymous CypA SNPs 351 published in the National Center for Biotechnology Information dbSNP database (www.ncbi.nlm.nih.gov/snp) a series of Huh-7.5 CypA mutant cell lines had been constructed comprising a CypA-Knockdown line (here: Huh-7.5sh-CypA-KD), a non-target control, (here: Huh-7.5sh-Ctr), a reconstituted CypA (here: Huh-7.5sh-CypA-KD+wt-CypA) and reconstituted SNP variant cell lines (here: Huh-7.5sh-CypA-KD+CypA[D66E]/[N106I]/[G96DHE134K]/[E84D]/[I89T]).

In a first approach we infected Huh-7.5 and Huh-7.5sh-CypA-KD cells with 229E-GFP virus at different MOIs and inspected virus-infected cells 24 and 48 hours p.I. by fluorescence microscopy. 229E-GFP virus infection (FIG. 8A) of Huh-7.5 cells strongly increased over time. Even at MOI 0.001 individual, infected cells appear at 48 h. In case of Huh-7.5sh-CypA-KD (FIG. 8B) only faint virus infection at 24 h with slight increase at 48 h can be found. This observation is confirmed by Western blot analysis of the 229E N protein at the 48 h time point. In Huh-7.5 cells N expression is strong even at MOI 0.001, whereas in the CypA-KD cells N protein is significantly diminished at MOI 0.1 and not detectable at MOI 0.001. In order to solidify these results obtained with the GFP-expressing 229E virus we infected the Huh-7.5 CypA mutant collection (see above) with 229E-LUC at MOI 0.1 utilizing Renilla luciferase protein expression as a measure of virus replication (FIG. 4). To characterize CypA expression levels of the various mutant cell lines (FIG. 4A) used in the Luciferase quantification experiments (FIG. 9B) we first performed qPCR analysis on CypA mRNA expression normalized to the TOP1 housekeeping gene mRNA. Although CypA mRNA levels were somewhat heterogeneous especially in the E84D mutant cell line, the knockdown in Huh-7.5sh-CypA-KD was about 96.7% as compared to Huh-7.5 cells.

As judged by Luciferase measurement (FIG. 9A) and 229E N protein analysis (FIG. 9B) virus replication in the CypA-KD cells was only minor as compared to Huh-7.5 or the non-target control (sh-Ctr) and CypA reconstituted (Huh-7.5sh-CypA-KD+CypA) cells. The similar LUC values of latter two indicate the lack of off-target effects of the CypA manipulation. But they also show the general impact of lentiviral mutation of cells, when compared to the significantly higher LUC expression in Huh-7.5. Most intriguingly, the CypA mutations 379

CypA[D66E]/[N106I]/[G96D] did not support 229E-LUC replication as opposed to the CypA[E134K]/[E84D]/[I89T] variants which is in close agreement with the HCV replication studies in these cell lines (28). As discussed by these authors the first three functional (with respect to suppression of virus replication) amino acid exchanges are located near the isomerase active site whereas the non-functional second mutation set is located remote. Destabilization of CypA was identified as the underlying mechanism, resulting in near-complete intracellular CypA depletion.

We have not shown this for HCoV-229E. However, it is intriguing to assume the same mechanism for the reduced and differential replicative behavior of the coronaviruses. Even so it could be expected that depletion or destabilization of the highly prominent CypA as a house-keeping gene would be detrimental to cell growth it is clear that the mutated Huh-7.5 cell lines proliferate quite normal. Reasons could be either that as opposed to a knockout the knockdown of CypA is not complete and the activity of the residual molecules suffices for cell growth or the PPIase functions can be overtaken by other isomerases as was already shown for prolyl isomerases of the Pin1 type (56, 57). In any case, CypA seems to be a prolyl isomerase required for propagation of HCV and CoVs. From both, the HCV and the present HCoV study it is clear that expression of correctly folded, stable CypA is essential for replication of both viruses. Genetic variation of host genes involved in virus infection and also in other human diseases (47) is of highest clinical interest as such proteins represent potential molecules for host-targeting therapeutic agents. Even in the case of rare genetic variants their analysis might give important clues to disease mechanism. For CoVs there are no host SNP data available which might give clues on resistance to or promotion of viral infection. In the case of HCV understanding the functional architecture of type III IFN genomic regions and SNPs have improved the knowledge on the pathogenetic mechanism of HCV infection (58). However, studying the effect of SNP mutations on infection has to be interpreted carefully considering composition of cohorts, differences in disease progression, or duration times of follow-up studies. For example, in the case of HIV-1 the rs8177826 SNP in the promoter region of the PPIA gene was reported in one study to promote acceleration to AIDS (59) and another study did not detect an effect of the SNP on disease progression or viral levels but rather was associated with a decreased risk of acquisition (60). We have shown earlier that SARS-CoV Nsp1 protein binds to cyclophilins. The binding of CypA to the SARS-CoV N protein is known from a very early educated guess finding using surface plasmon resonance biosensor technology (61). This is supported by a spectrometric profiling study showing the incorporation of CypA into SARS-CoV virions (62). It can thus be speculated that CoV inhibition is a direct consequence of blockade of the N capsid protein 413 required for replication and packaging of viral RNA genome by CsA derivative/CypA complexes. It further remains to be determined whether other coronaviral proteins require the proline-directed binding and PPIase activity of CypA. It seems to be clear, however, that non-immunosuppressive CsA derivatives block CoV replication and ALV and NIM811, which have already been tested in human phase III (ALV) or II trials (NIM811) as well as new CsA position 1-modified compounds are promising candidate HTAs for anti-coronaviral therapy.

In another aspect it was found that cyclosporin A derivatives Alisporivir and NIM 811 have the potential to inhibit feline and murine Coronaviruses. This was unexpected as various cyclosporin A derivatives have been tested with various viruses but activity was unpredictable. This might be due to the fact that the proteins involved in the mechanism, such as non-structural proteins (nsp), are very variable between species. There is no treatment until now for feline and murine Coronavirus infections. These infections are often fetal and a treatment is highly desirable. On the one hand, felidae Coronaviruses are highly pathogenic and ailment is looked for. On the other hand murine Coronaviruses are detrimental when laboratory animals are infested.

Figure 10A:
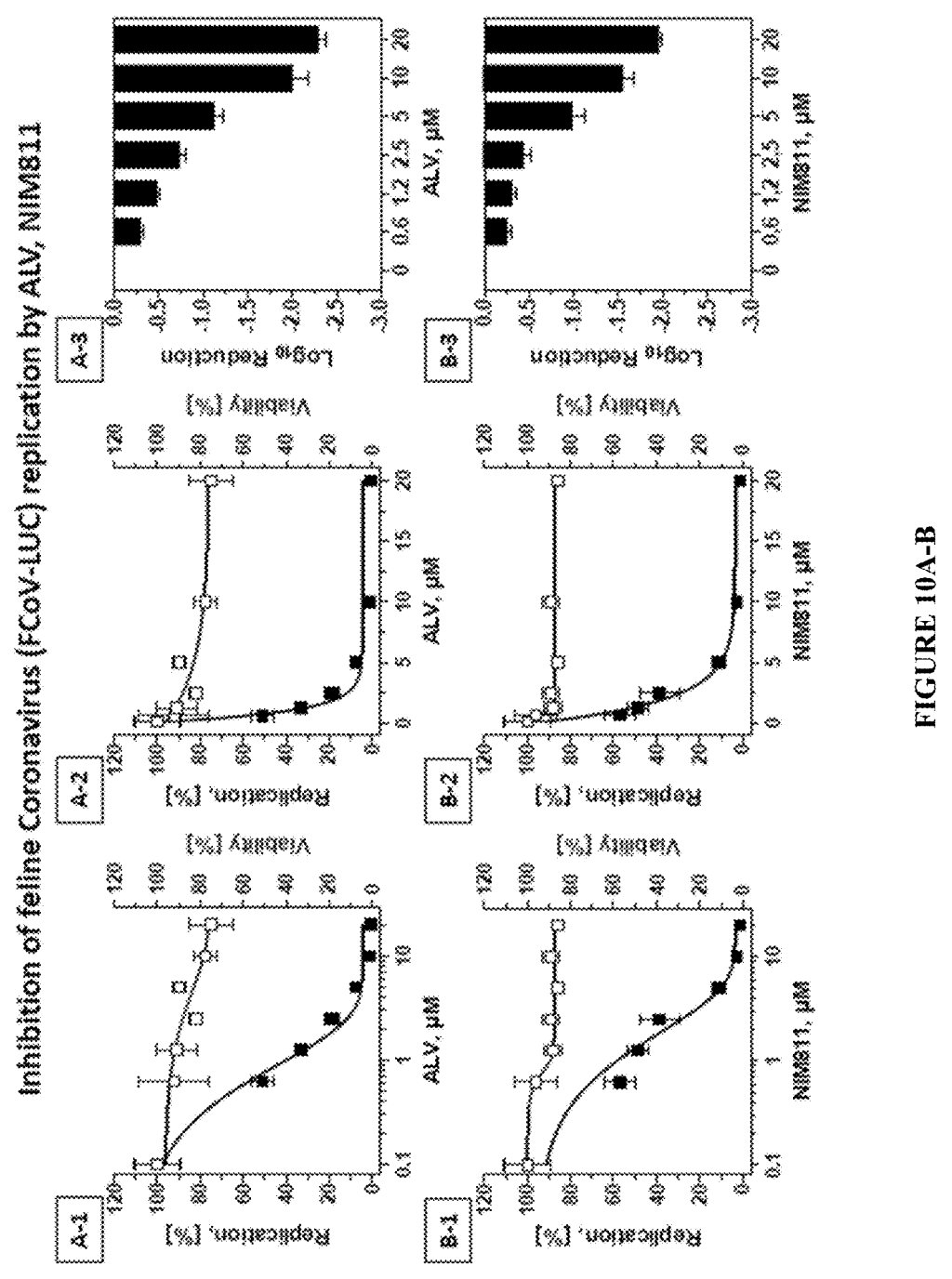
Figure 11A:
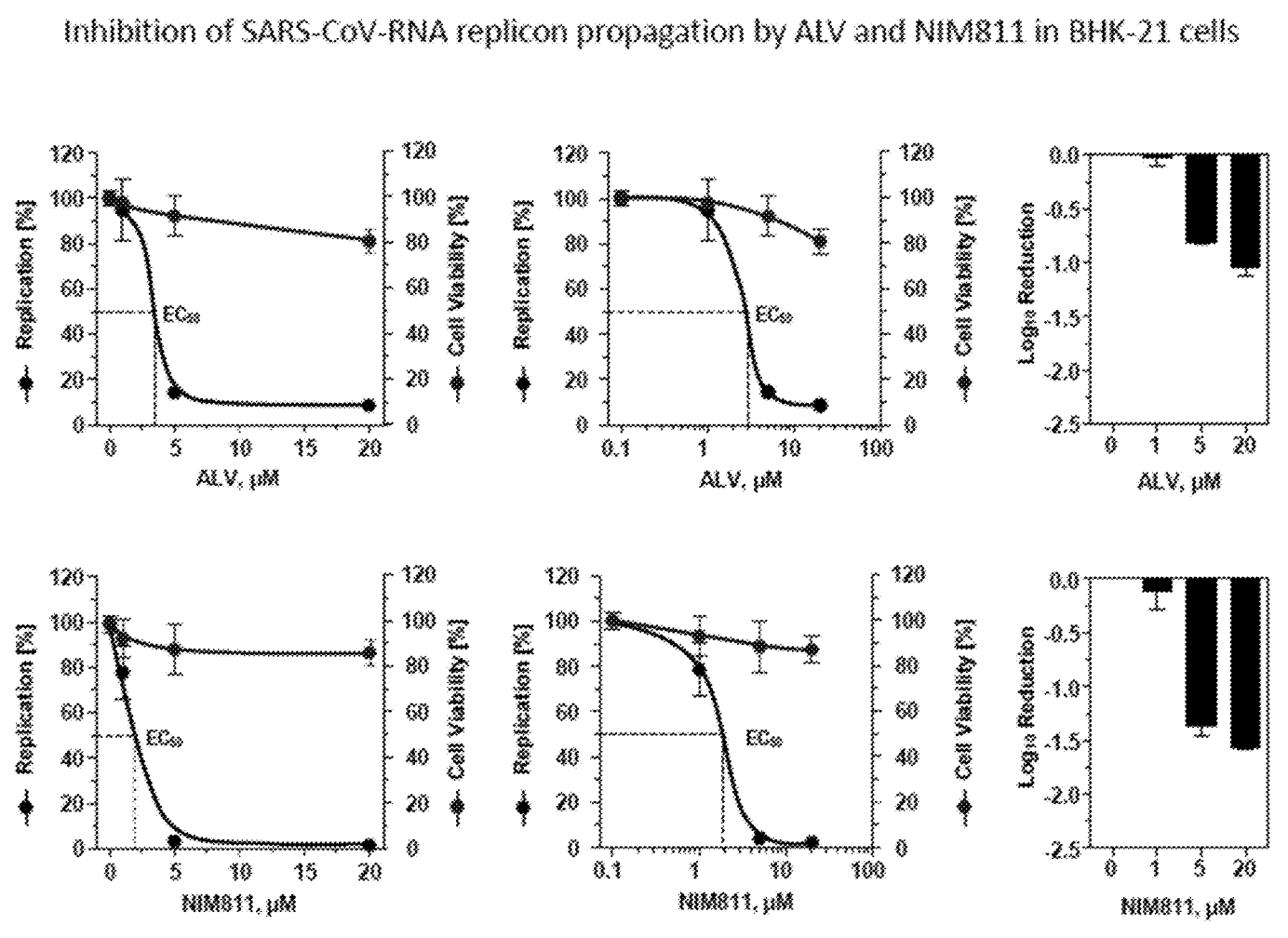
Figure 11B:
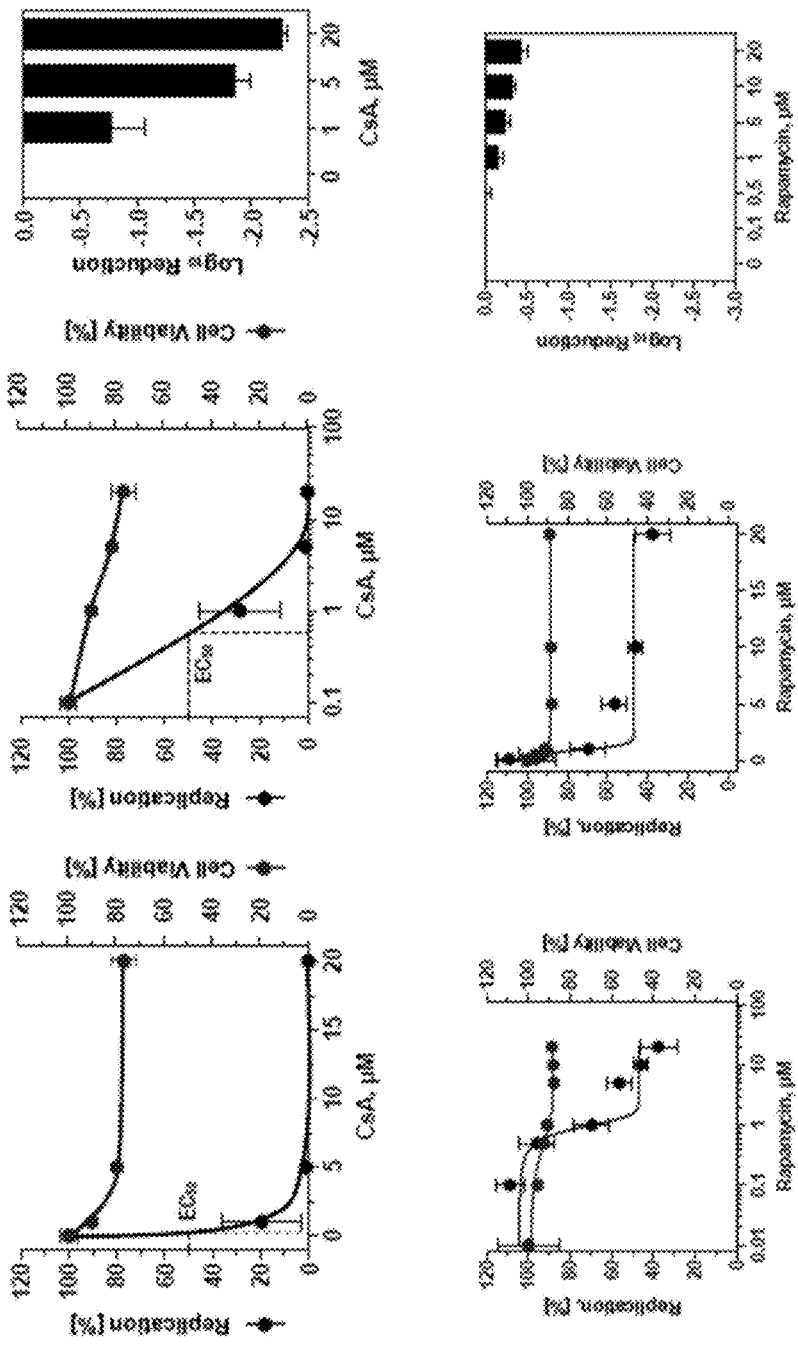
Figure 12C:
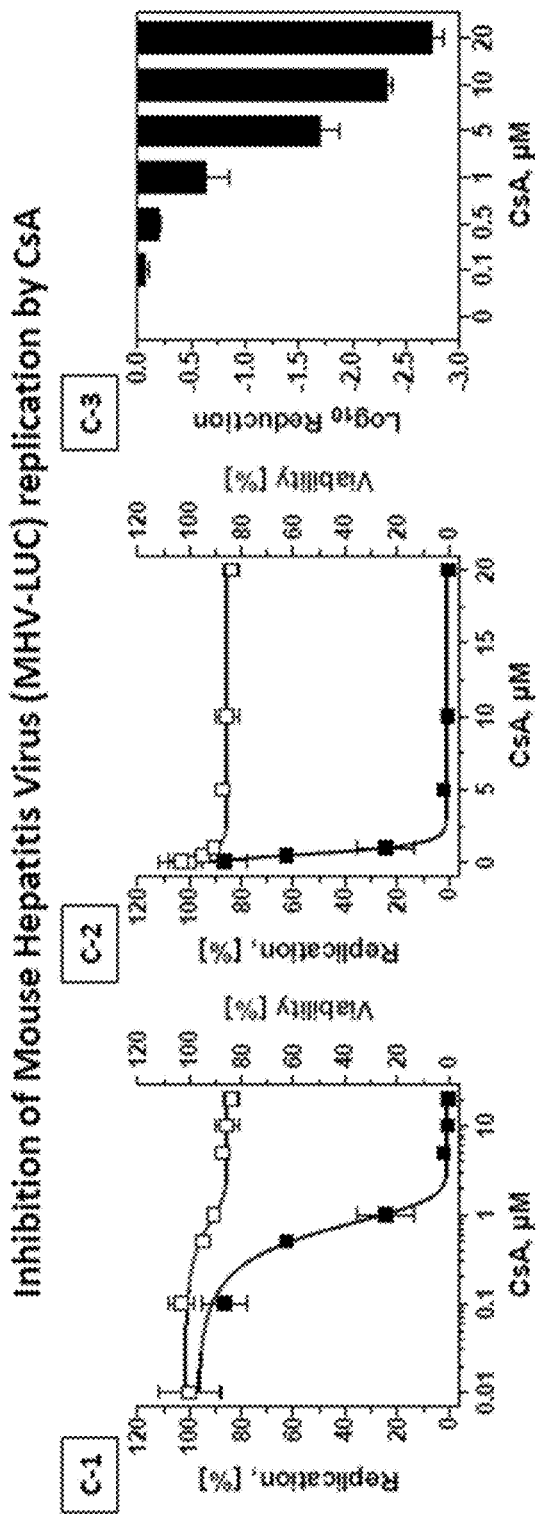

The present invention provides an active agent, a composition and a method for treating feline and murine Coronavirus infections. It has been found that Alisporivir and NIM 811 in micromolar concentration inhibits spread of these viruses without being detrimental to the cells to be protected, as is shown in FIGS. 10-12.

REFERENCES

1. Perlman S, Netland J. 2009. Coronaviruses post-SARS: update on replication and pathogenesis. NatRevMicrobiol 7:439-450.
2. Stadler K, Masignani V, Eickmann M, Becker S, Abrignani S, Klenk H D, Rappuoli R. 2003. SARS—beginning to understand a new virus. Nat Rev Microbiol 1:209-218.
3. van der Hoek L, Pyrc K, Jebbink M F, Vermeulen-Oost W, Berkhout R J, Wolthers
K C, Wertheim-van Dillen P M, Kaandorp J, Spaargaren J, Berkhout B. 2004. Identification of a new human coronavirus. Nat Med 10:368-373.
4. Woo P C, Lau S K, Chu C M, Chan K H, Tsoi H W, Huang Y, Wong B H, Poon R W,
Cai J J, Luk W K, Poon L L, Wong S S, Guan Y, Peiris J S, Yuen K Y. 2005. Characterization and complete genome sequence of a novel coronavirus, coronavirus HKU1, from patients with pneumonia. J Virol 79:884-895.
5. WHO. 2014. WHO Global Alert and Response, Update 15: summary and literature update as of 9 May 2014 http://www.whoint/csr/disease/coronavirus_infections/MERS_CoV_Update_09 M ay_2014. pdf?ua=1.
6. Dijkman R, Jebbink M F, El Idrissi N B, Pyrc K, Muller M A, Kuijpers T W, Zaaijer
HL, van der Hoek L. 2008. Human coronavirus NL63 and 229E seroconversion in children. J Clin Microbiol 46:2368-2373.
7. Dijkman R, Jebbink M F, Gaunt E, Rossen J W, Templeton K E, Kuijpers T W, van
der Hoek L. 2012. The dominance of human coronavirus OC43 and NL63 infections in infants. J Clin Virol 53:135-139.
8. Gaunt E R, Hardie A, Claas E C, Simmonds P, Templeton K E. 2010. Epidemiology
and clinical presentations of the four human coronaviruses 229E, HKU1, NL63, and OC43 detected over 3 years using a novel multiplex real-time PCR method. J Clin Microbiol 48:2940-2947.
9. Sims A C, Burkett S E, Yount B, Pickles R J. 2008. SARS-CoV replication and pathogenesis in an in vitro model of the human conducting airway epithelium. Virus Res 133:33-44.
10. Arbour N, Day R, Newcombe J, Talbot P J. 2000. Neuroinvasion by human respiratory coronaviruses. J Virol 74:8913-8921.
11. Collins A R. 2002. In vitro detection of apoptosis in monocytes/macrophages infected
with human coronavirus. Clin Diagn Lab Immunol 9:1392-1395.
12. Desforges M, Miletti T, Gagnon M, Talbot PJ. 2006. HCoV-229E infects and activates monocytes. Adv Exp Med Biol 581:511-514.
13. Mesel-Lemoine M, Millet J, Vidalain P O, Law H, Vabret A, Lorin V, Escriou N,
Albert M L, Nal B, Tangy F. 2012. A human coronavirus responsible for the common cold massively kills dendritic cells but not monocytes. J Virol 86:7577-7587.
14. de Wilde A H, Jochmans D, Posthuma C C, Zevenhoven-Dobbe J C, van Nieuwkoop
S, Bestebroer $T_M$, van den Hoogen B G, Neyts J, Snijder E J. 2014. Screening of an FDA-Approved Compound Library Identifies Four Small-Molecule Inhibitors of Middle East Respiratory Syndrome Coronavirus Replication in Cell Culture. Antimicrobial Agents and Chemotherapy 58:4875-4884.
15. Dyall J, Coleman C M, Hart B J, Venkataraman T, Holbrook M R, Kindrachuk J,
Johnson R F, Olinger G G, Jahrling P B, Laidlaw M, Johansen L M, Lear-Rooney C M, Glass P J, Hensley L E, Frieman M B. 2014. Repurposing of Clinically Developed
Drugs for Treatment of Middle East Respiratory Syndrome Coronavirus Infection.
Antimicrobial Agents and Chemotherapy 58:4885-4893.
16. LaFemina R L. 2014. Alternative Screening Approaches for Discovery of MERS Chemother Coronavirus Inhibitors. Antimicrobial Agents and apy doi:10.1128/aac.03406-14.
17. Adedeji A O, Singh K, Kassim A, Coleman C M, Elliott R, Weiss S R, Frieman M B,
Sarafianos S G. 2014. Evaluation of SSYA10-001 as a Replication Inhibitor of Severe Acute Respiratory Syndrome, Mouse Hepatitis, and Middle East Respiratory Syndrome Coronaviruses. Antimicrobial Agents and Chemotherapy 58:4894-4898.
18. Lundin A, Dijkman R, Bergstrom T, Kann N, Adamiak B, Hannoun C, Kindler E,
Jonsdottir H R, Muth D, Kint J, Forlenza M, Muller M A, Drosten C, Thiel V, Trybala E. 2014. Targeting membrane-bound viral RNA synthesis reveals potent inhibition of diverse coronaviruses including the middle East respiratory syndrome virus. PLoS Pathog 10:e1004166.
19. Pfefferle S, Schopf J, Kogl M, Friedel C C, Muller M A, Carbajo-Lozoya J, Stellberger T, von Dall'Armi E, Herzog P, Kallies S, Niemeyer D, Ditt V, Kuri T, Zust R, Pumpor K, Hilgenfeld R, Schwarz F, Zimmer R, Steffen I, Weber F, Thiel V, Herrler G, Thiel H J, Schwegmann-Wessels C, Pohlmann S, Haas J, Drosten C, von Brunn A. 2011. The SARS-coronavirus-host interactome: identification of cyclophilins as target for pan-coronavirus inhibitors. PLoS Pathog 7:e1002331.
20. Carbajo-Lozoya J, Ma-Lauer Y, Malešević M, Theuerkorn M, Kahlert V, Prell E,
von Brunn B, Muth D, Baumert T F, Drosten C, Fischer G, von Brunn A. 2014.
Human coronavirus NL63 replication is cyclophilin A-dependent and inhibited by non-immunosuppressive cyclosporine A-derivatives including Alisporivir. Virus Res 184:44-53.
21. de Wilde A H, Li Y, van der Meer Y, Vuagniaux G, Lysek R, Fang Y, Snijder E J,
van Hemert M J. 2013. Cyclophilin Inhibitors Block Arterivirus Replication by Interfering with Viral RNA Synthesis. Journal of Virology 87:1454-1464.
22. de Wilde A H, Raj V S, Oudshoorn D, Bestebroer $T_M$, van Nieuwkoop S, Limpens
R W, Posthuma C C, van der Meer Y, Barcena M, Haagmans B L, Snijder E J, van den Hoogen B G. 2013. MERS-coronavirus replication induces severe in vitro cytopathology and is strongly inhibited by cyclosporin A or interferon-alpha treatment. J Gen Virol 94:1749-1760.
23. de Wilde A H, Zevenhoven-Dobbe J C, van der Meer Y, Thiel V, Narayanan K, Makino S, Snij der E J, van Hemert M J. 2011. Cyclosporin A inhibits the replication of diverse coronaviruses. J Gen Virol 92:2542-2548.
24. Sastre P, Dijkman R, Camuñas A, Ruiz T, Jebbink M F, van der Hoek L, Vela C, . Rueda P. 2011. Differentiation between Human Coronaviruses NL63 and 229E Using a
Novel Double-Antibody Sandwich Enzyme-Linked Immunosorbent Assay Based on Specific Monoclonal Antibodies. Clinical and Vaccine Immunology 18:113-118.
25. Whitaker C, Caspe S. 2011. Synthesis of Cyclosporin H. US20120253007 A1.
26. Malešević M, Gutknecht D, Prell E, Klein C, Schumann M, Nowak R A, Simon J C, Schiene-Fischer C, Saalbach A. 2013. Anti-inflammatory effects of extracellular cyclosporine are exclusively mediated by CD147. J Med Chem 56:7302-7311.
27. Blight K J, McKeating J A, Rice C M. 2002. Highly permissive cell lines for subgenomic and genomic hepatitis C virus RNA replication. J Virol 76:13001-13014.
28. von Hahn T, Schiene-Fischer C, Van N D, Pfaender S, Karavul B, Steinmann E, Potthoff A, Strassburg C, Hamdi N, Abdelaziz A I, Sarrazin C, Muller T, Berg T, Trepo E, Wedemeyer H, Manns M P, Pietschmann T, Ciesek S. 2012. Hepatocytes that express variants of cyclophilin A are resistant to HCV infection and replication. Gastroenterology 143:439-447 e431.
29. Feigelstock D A, Mihalik K B, Kaplan G, Feinstone S M. 2010. Increased susceptibility of Huh7 cells to HCV replication does not require mutations in RIG-I. Virol J 7:44.
30. Koutsoudakis G, Herrmann E, Kallis S, Bartenschlager R, Pietschmann T. 2007.
The Level of CD81 Cell Surface Expression Is a Key Determinant for Productive Entry of Hepatitis C Virus into Host Cells. Journal of Virology 81:588-598.
31. Cervantes-Barragan L, Zust R, Maier R, Sierro S, Janda J, Levy F, Speiser D, Romero P, Rohrlich P S, Ludewig B, Thiel V. 2010. Dendritic cell-specific antigen delivery by coronavirus vaccine vectors induces long-lasting protective antiviral and antitumor immunity. MBio 1.
32. Carbajo-Lozoya J, Muller M A, Kallies S, Thiel V, Drosten C, von Brunn A. 2012.
Replication of human coronaviruses SARS-CoV, HCoV-NL63 and HCoV-229E is inhibited by the drug FK506. Virus Res 165:112-117.
33. Bartenschlager R, Pietschmann T. 2005. Efficient hepatitis C virus cell culture system: what a difference the host cell makes. Proc Natl Acad Sci USA 102:9739-9740.
34. Raj V S, Mou H, Smits S L, Dekkers D H, Muller M A, Dijkman R, Muth D, Demmers J A, Zaki A, Fouchier R A, Thiel V, Drosten C, Rottier P J, Osterhaus A D,
Bosch B J, Haagmans B L. 2013. Dipeptidyl peptidase 4 is a functional receptor for the emerging human coronavirus-EMC. Nature 495:251-254.
35. Friebe P, Boudet J, Simorre J P, Bartenschlager R. 2005. Kissing-loop interaction in
the 3' end of the hepatitis C virus genome essential for RNA replication. J Virol 79:380-392.
36. de Paulis A, Ciccarelli A, de Crescenzo G, Cirillo R, Patella V, Marone G. 1996.
Cyclosporin H is a potent and selective competitive antagonist of human basophil activation by N-formyl-methionyl-leucyl-phenylalanine Journal of Allergy and Clinical Immunology 98:152-164.
37. LeGrue S, Turner R, Weisbrodt N, Dedman. 1986. Does the binding of cyclosporine
to calmodulin result in immunosuppression? Science 234:68-71.
38. Huang S, Bjornsti M A, Houghton P J. 2003. Rapamycins: mechanism of action and
cellular resistance. Cancer Biol Ther 2:222-232.
39. Ge X Y, Li J L, Yang X L, Chmura A A, Zhu G, Epstein J H, Mazet J K, Hu B, Zhang
W, Peng C, Zhang Y J, Luo C M, Tan B, Wang N, Zhu Y, Crameri G, Zhang S Y, Wang L F, Daszak P, Shi Z L. 2013. Isolation and characterization of a bat SARS-like coronavirus that uses the ACE2 receptor. Nature 503:535-538.
40. Huynh J, Li S, Yount B, Smith A, Sturges L, Olsen J C, Nagel J, Johnson J B, Agnihothram S, Gates J E, Frieman M B, Baric R S, Donaldson E F. 2012. Evidence supporting a zoonotic origin of human coronavirus strain NL63. J Virol 86:12816-12825.
41. Pfefferle S, Oppong S, Drexler J F, Gloza-Rausch F, Ipsen A, Seebens A, Muller
M A, Annan A, Vallo P, Adu-Sarkodie Y, Kruppa T F, Drosten C. 2009. Distant relatives of severe acute respiratory syndrome coronavirus and close relatives of human coronavirus 229E in bats, Ghana. Emerg Infect Dis 15:1377-1384.
42. Vijgen L, Keyaerts E, Moes E, Thoelen I, Wollants E, Lemey P, Vandamme A M,
Van Ranst M. 2005. Complete genomic sequence of human coronavirus OC43: molecular clock analysis suggests a relatively recent zoonotic coronavirus transmission event. J Virol 79:1595-1604.
43. Hemida M G, Perera R A, Wang P, Alhammadi M A, Siu L Y, Li M, Poon L L, Saif
L, Alnaeem A, Peiris M. 2013. Middle East Respiratory Syndrome (MERS) coronavirus seroprevalence in domestic livestock in Saudi Arabia, 2010 to 2013. Euro Surveill 18:20659.
44. Reusken C B, Haagmans B L, Muller M A, Gutierrez C, Godeke G J, Meyer B, Muth
D, Raj V S, Smits-De Vries L, Corman V M, Drexler J F, Smits S L, El Tahir Y E, De Sousa R, van Beek J, Nowotny N, van Maanen K, Hidalgo-Hermoso E, Bosch B J, Rottier P, Osterhaus A, Gortazar-Schmidt C, Drosten C, Koopmans M P. 2013. Middle East respiratory syndrome coronavirus neutralising serum antibodies in dromedary camels: a comparative serological study. Lancet Infect Dis 13:859-866.
45. van Hemert M J, de Wilde A H, Gorbalenya A E, Snijder E J. 2008. The in vitro RNA
synthesizing activity of the isolated arterivirus replication/transcription complex is dependent on a host factor. J Biol Chem 283:16525-16536.
46. Lang K, Schmid F X, Fischer G. 1987. Catalysis of protein folding by prolyl isomerase. Nature 329:268-270.
47. Nigro P, Pompilio G, Capogrossi M C. 2013. Cyclophilin A: a key player for human
disease. Cell Death Dis 4:e888.
48. Lin K, Gallay P. 2013. Curing a viral infection by targeting the host: the example of cyclophilin inhibitors. Antiviral Res 99:68-77.
49. Naoumov N V. 2014. Cyclophilin inhibition as potential therapy for liver diseases. J Hepatol 61:1166-1174.
50. Gallay P A, Lin K. 2013. Profile of alisporivir and its potential in the treatment of hepatitis C. Drug Des Devel Ther 7:105-115.
51. Membreno F E, Espinales J C, Lawitz E J. 2013. Cyclophilin inhibitors for hepatitis C
therapy. Clin Liver Dis 17:129-139.
52. Hopkins S, Scorneaux B, Huang Z, Murray M G, Wring S, Smitley C, Harris R, Erdmann F, Fischer G, Ribeill Y. 2010. SCY-635, a novel nonimmunosuppressive analog of cyclosporine that exhibits potent inhibition of hepatitis C virus RNA replication in vitro. Antimicrob Agents Chemother 54:660-672.
53. Sanglier J J, Quesniaux V, Fehr T, Hofmann H, Mahnke M, Memmert K, Schuler W, Zenke G, Gschwind L, Maurer C, Schilling W. 1999. Sanglifehrins A, B, C and D, novel cyclophilin-binding compounds isolated from *Streptomyces* sp. A92-308110. I. Taxonomy, fermentation, isolation and biological activity. J Antibiot (Tokyo) 52:466-473
54. Prell E, Kahlert V, Rucknagel K P, Malešević M, Fischer G. 2013. Fine tuning the
inhibition profile of cyclosporine A by derivatization of the MeBmt residue.
Chembiochem 14:63-65.
55. Zhou D, Mei Q, Li J, He H. 2012. Cyclophilin A and viral infections. Biochem Biophys Res Commun 424:647-650.
56. Gemmill T R, Wu X, Hanes S D. 2005. Vanishingly low levels of Ess1 prolyl-isomerase
activity are sufficient for growth in *Saccharomyces cerevisiae*. J Biol Chem 280:15510-15517.
57. Arevalo-Rodriguez M, Cardenas M E, Wu X, Hanes S D, Heitman J. 2000. Cyclophilin A and Ess1 interact with and regulate silencing by the Sin3-Rpd3 histone deacetylase. EMBO J 19:3739-3749.
58. Riva E, Scagnolari C, Turriziani 0, Antonelli G. 2014. Hepatitis C virus and interferon type III (interferon lambda 3/interleukin 28B and interferon lambda 4): genetic basis of susceptibility to infection and response to antiviral treatment. Clinical Microbiology and Infection doi:10.1111/1469-0691.12797:n/a-n/a.
59. An P, Wang L H, Hutcheson-Dilks H, Nelson G, Donfield S, Goedert J J, Rinaldo
C R, Buchbinder S, Kirk G D, O'Brien S J, Winkler C A. 2007. Regulatory polymorphisms in the cyclophilin A gene, PPIA, accelerate progression to AIDS. PLoS Pathog 3:e88.
60. Bigham A W, Mackelprang R D, Celum C, De Bruyn G, Beima-Sofie K, John-Stewart G, Ronald A, Mugo N R, Buckingham K, Bamshad M J, Mullins J I, McElrath M J, Lingappa J R. 2014. Variants in host viral replication cycle genes are associated with heterosexual HIV-1 acquisition in Africans. J Acquir Immune Defic Syndr 66:127-134.
61. Luo C, Luo H, Zheng S, Gui C, Yue L, Yu C, Sun T, He P, Chen J, Shen J, Luo X,
Li Y, Liu H, Bai D, Yang Y, Li F, Zuo J, Hilgenfeld R, Pei G, Chen K, Shen X, Jiang H. 2004. Nucleocapsid protein of SARS coronavirus tightly binds to human cyclophilin A. BiochemBiophysResCommun 321:557-565.
62. Neuman B W, Joseph J S, Saikatendu K S, Serrano P, Chatterjee A, Johnson M A,
Liao L, Klaus J P, Yates J R, III, Wuthrich K, Stevens R C, Buchmeier M J, Kuhn P. 2008. Proteomics analysis unravels the functional repertoire of coronavirus nonstructural protein 3 2. JVirol 82:5279-5294.

What is claimed is:

1. A method for treating a Coronavirus infection in a patient comprising administering to a patient with a Coronavirus infection an effective amount of a non-immunosuppresant cyclophilin inhibitor.

2. The method of claim 1, wherein the non-immunosuppressant cyclophilin inhibitor is selected from alisporivir and NIM811.

3. The method of claim 2, further comprising administering a direct acting antiviral agent.

4. A method of claim 3, wherein the direct acting antiviral agent is ribavirin.

5. The method of claim 1, wherein the Coronavirus is selected from SARS-CoV (Severe Acute Respiratory Syndrome-Corona Virus), and CoV MERS (Middle East Respiratory Syndrome virus).

6. A method for treating a Coronavirus infection in a feline subject or a murine subject comprising administering to a feline subject or a murine subject with a Coronavirus infection an effective amount of a non-immunosuppressant cyclophilin inhibitor selected from alisporivir and NIM811 or a mixture thereof.

7. The method of claim 6, further comprising administering a direct antiviral agent.

8. A method according to claim 6, wherein the Coronavirus is selected from feline Coronavirus (FCoV), or Mouse Hepatitis Virus (MHV-LUC).

\* \* \* \* \*